(12) United States Patent
Burkart et al.

(10) Patent No.: US 7,727,738 B2
(45) Date of Patent: Jun. 1, 2010

(54) METHODS FOR GENERATING ANALOGS OF COENZYME A

(75) Inventors: Michael D. Burkart, San Diego, CA (US); Kristine Clarke, San Diego, CA (US); Andrew L Mercer, La Jolla, CA (US); James J. LaClair, San Diego, CA (US); Jordan Meier, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 250 days.

(21) Appl. No.: 11/485,247

(22) Filed: Jul. 11, 2006

(65) Prior Publication Data
US 2007/0128683 A1     Jun. 7, 2007

Related U.S. Application Data

(60) Provisional application No. 60/698,333, filed on Jul. 11, 2005.

(51) Int. Cl.
*C12Q 1/34* (2006.01)
*C12P 21/06* (2006.01)
*C12N 9/00* (2006.01)
*C07H 21/04* (2006.01)

(52) U.S. Cl. .................. 435/18; 435/68.1; 435/183; 536/23.2

(58) Field of Classification Search .................. None
See application file for complete search history.

(56) References Cited

OTHER PUBLICATIONS

Nazi et al. Anal Biochem. Jan. 1, 2004;324(1):100-5.*
La Clair et al. Chem Biol. Feb. 2004;11(2):195-201.*
Keating et al. Biochemistry. Dec. 19, 2000;39(50):15513-21.*
Abiko, "Investigations on Pantothenic Acid and Its Related Compounds," *Biochem*, 1967, 61(3), 290-299.
Alexander et al., "Mechanism of Carbamate Inactivation of FAAH: Implications for the Design of Covalent Inhibitors and In Vivo Functional Probes for Enzymes," *Chem Biol.*, 2005, 12, 1179-1187.
Bertozzi et al., "Chemistry in living systems," *Nat. Chem Biol.*, 2005, 1(1), 13-21.
Burns et al., "Iso-coenzyme A," *J. Biol. Chem.*, 2005, 280(17), 16550-16558.
Chen et al., "Site-specific labeling of proteins with small molecules in live cells," *Curr Opin Biotechnol.*, 2005, 16, 35-40.
Clarke et al., "In Vivo Reporter Labeling of Proteins via Metabolic Delivery of Coenzyme Analogues," *J. Am. Chem. Soc.*, 2005, 127, 11234-11235.
Cook et al., "Chemical Approaches to the Investigation of Cellular Systems," *C.R. Bioorg. Med. Chem.*, 2002, 10, 829-840.
Daugherty et al., "Complete Reconstitution of the Human Coenzyme a Biosynthetic Pathway via Comparative Genomics," *Biol. Chem.*, 2002, 277(24), 21431-21439.
Dueno et al., "Cesium Promoted *O*-Alkylation of Alcohols for the Efficient Ether Synthesis," *Tet. Lett.*, 1999, 40, 1843-1846.

Fritze et al., "Epitope Tagging: General Method for Tracking Recombinant Proteins," *Meth. Enzymol.*, 2000, 327, 3-16.
George et al., "Specific Labeling of Cell Surface Proteins with Chemically Diverse Compounds," *J. Am. Chem Soc.*, 2004, 126, 8896-8897.
Ivey et al., "The Structure of the Pantothenate Kinase ADP-Pantothenate Ternary Complex Reveals the Relationship between the Binding Sites for Substrate, Allosteric Regulator, and Antimetabolites," J. Biol. Chem., 2004, 279(34), 35622-35629.
Jackowski et al., "Regulation of Coenzyme A Biosynthesis," *J Bacteriol.*, 1981, 148(3), 926-932.
Jackowski et al., "Cloning, Sequence, and Expression of the Pantothenate Permease (*panF*) Gene of *Escherichia coli*," *J. Bacteriol.*, 1990, 172(7), 3842-3848.
Jenni, S. et al., "Architecture of Mammalian Fatty Acid Synthase at 4.5 Å Resolution," *Science*, 2006, 311, 1258-1262.
Khidekel et al., "Exploring the *O*-GlcNAc proteome: Direct identification of *O*-GlcNAc-modified proteins from the brain," *Proc. Natl. Acad. Sci. U.S.A.*, 2004, 101(36), 13132.
Kohn et al., "The Staudinger Ligation—A Gift to Chemical Biology," *Angew. Chem. Int. Ed. Engl.*, 2004, 43, 3106-3116.
Krause et al., "Syntheses of Pantolactone and Pantothenic Acid Derivatives as Potential Lipid Regulating Agents," *Syn. Comm.*, 2006, 36, 365-391.
Kumar et al., "A Solid-Phase Synthetic Strategy for Labeled Peptides: Synthesis of a Biotinylated Derivative of the δ Opioid Receptor Antagonist TIPP (Tyr-Tic-Phe-Phe-OH)," *Org. Lett.*, 2003, 5(5), 613-616.
Kupke et al., "4'-Phosphopantetheine and Coenzyme A Biosynthesis in Plants," *Biol. Chem.*, 2003, 278(40), 38229.
La Clair et al., "A Central Strategy for Converting Natural Products into Flourescent Probes," *ChemBioChem*, 2006, 7, 409-416.
La Clair et al., "Manipulation of Carrier Proteins in Antibiotic Biosynthesis," *M.D. Chem Biol.*, 2004, 11, 195-201.
Lippincott-Schwartz et al., "Developmental and Use of Fluorescent Protein Markers in Living Cells," *Science*, 2003, 300, 87-91.
Mahal et al, "Engineering Chemical Reactivity on Cell Surfaces Through Oligosaccharide Biosythesis," *C.R. Science*, 1997, 276, 1125-1128.
Maier et al., "Architecture of a Fungal Fatty Acid Synthase at 5 Å Resolution," *Science*, 2006, 311, 1263-1267.
Mandel et al., "Modular Synthesis of Pantetheine and Phosopantetheine," *Org. Lett.*, 2004, 6(26), 4801-4803.
Martin et al., "Separate Enzymes Catalyze the Final Two Steps of Coenzyme A Biosynthesis in *Brevibacterium ammoniagenes*: Puri (Continued)

*Primary Examiner*—Christian L Fronda
(74) *Attorney, Agent, or Firm*—Fenwick & West LLP

(57) ABSTRACT

Methods to generate analogs of coenzyme A in vitro and in vivo are disclosed. The methods comprise reacting pantetheine or a derivative thereof with a reporter to form labeled pantetheine or a derivative thereof, phosphorylating the labeled pantetheine or derivative thereof to form phosphopantetheine or a derivative thereof, adenylating the labeled phosphopantetheine or derivative thereof to form a labeled dephosphoCoenzyme A or derivative thereof, and phosphorylating the 3'-hydrozyl of the labeled dephosphoCoenzume A or derivative thereof to form a labeled coenzyme A analog or derivative thereof.

27 Claims, 11 Drawing Sheets

OTHER PUBLICATIONS fication of Pantetheine Phosphate Adenylyltranferase," *Biochem. Biophys. Res. Commun.*, 1993, 192(3), 1155-1161.

Martin et al., "Synthesis of Novel Analogs of Acetyl Coenzyme A: Mimics of Enzyme Reaction Intermediates," *J.Am. Chem. Soc.*, 1994, 116, 4660-4668.

Massoud et al., "Molecular imaging in living subjects: seeing fundamental biological processes in a new light," *Genes Dev.*, 2003, 17, 545-580.

Mercer et al., "Fluorescent Multiplex Analysis of Carrier Protein Post-Translational Modification," *ChemBioChem.*, 2005, 6, 1335-1337.

Michelson, "Synthesis of Coenzyme A," *Biochim. Biophys. Acta*, 1964, 93, 71-77.

Mishra et al., "Identification of *yacE* (*coaE*) as the Structural gene for Dephosphocoenzyme A Kinase in *Escherichia coli* K-12," *Bacteriol.*, 2001, 183(9), 2774-2778.

Mishra et al., "Coenzyme A Analogues and Derivatives: Synthesis and Applications as Mechanistic Probes of Coenzyme A Ester-Utilizing Enzymes," *Chem Rev.*, 2000, 100(9), 3283-3309.

Moffatt et al., "Nucleoside Polyphosphates, XII: The Total Synthesis of Coenzyme A$^2$," *J. Am. Chem. Soc.*, 1961, 83, 663-675.

Nazi et al., "One-pot chemoenzymatic preparation of coenzyme A analogues," *Anal. Biochem.*, 2004, 324, 100-105.

Pugh, E.L. et al., "Studies on the Mechanism of Fatty Acid Synthesis," *J, Biol. Chem.*, 1965, 240(12), 4727-4733.

Rock et al., "Pantothenate Kinase Regulation of the Intracellular Concentration of Coenzyme A," *J. Biol. Chem.*, 2000, 275(2), 1377-1383.

Rudik et al., "4-Hydroxycinnamyl-CoA: An Ionizable Probe of the Active Site of the Medium Chain- Acyl-CoA Dehydrogenase," *Biochemistry*, 2000, 39, 92-101.

Saxon et al., "Cell Surface Engineering by a Modified Staudinger Reaction," *Science*, 2000, 287, 2007-2010.

Schwartz et al., "α-Fluoro Acid and α-Fluoro Amide Analogs of Acetyl-CoA as Inhibitors of Citrate Synthase: Effect of p$K_a$ Matching on Binding Affinity and Hydrogen Bond Length," *Biochemistry*, 1995, 34, 15459-15466.

Silva et al., "Valproyl-DephosphocoA: A Novel Metabolite of Valproate Formed In Vitro in Rat Liver Mitochondria," *Drug Metabolism Disposition*, 2004, 32, 1304-1310.

Speers et al., "Profiling Enzyme Activities In Vivo Using Click Chemistry Methods," *Chem. Biol.*, 2004, 11, 535-546.

Speers et al., "Activity-Based Protein Profiling in Vivo Using a Copper (I)-Catalyzed Axide-Alkyne [3+2] Cycloaddition," *J. Am. Chem. Soc.*, 2003, 125, 4686-4687.

Strauss et al., "Phosphopantothenoylcysteine Synthetase from *Escherichia coli*," *Biol. Chem.*, 2001, 276(17), 13513-13516.

Strauss et al., "The Antibiotic Activity of N-Pentylpantothenamide Results from Its Conversion to Ethyldetheia-Coenzyme A, a Coenzyme A Antimetabolite," *J. Biol. Chem.*, 2002, 277(50), 48205-48209.

Tai et al., "Parallel Identification of *O*-GlcNAc-Modified Proteins from Cell Lysates," *J. Am. Chem. Soc.*, 2004, 126, 10500-10501.

Tsien, "The Green Fluorescent Protein," *Annu. Rev. Biochem.*, 1998, 67, 509-544.

Virga et al., "Structure-activity relationships and enzyme inhibition of pantothenamide-type pantothenate kinase inhibitors," *Bioorg. Med. Chem.*, 2006, 14, 1007-1020.

Vivero-Pol et al., "Multicolor Imaging of Cell Surface Proteins," *J. Am. Chem. Soc.*, 2005, 127, 12770-12771.

Witkowski et al., "Structural organization of the multifunctional animal fatty-acid synthase," *Eur. J. Biochem.*, 1991, 198, 571-579.

Worrall et al., "A bifunctional enzyme complex in coenzyme A biosynthesis: purification of pantetheine phosphate adenylyltransferase and dephospho-CoA kinase," *Biochem.*, 1983, 215, 153-157.

Worthington et al., "One-pot chemo-enzymatic synthesis of reporter-modified proteins," *Org. Biomol. Chem.*, 2005, 4, 44-46.

Yarema et al., "Metabolic Delivery of Ketone Groups to Sialic Acid Residues," *J. Biol. Chem.*, 1998, 273(47), 31168-31179.

Yin et al., "Phagemid Encoded Small Molecules for High Throughput Screening of Chemical Libraries," *J. Am. Chem. Soc.*, 2004, 126, 13570-13571.

Yin et al., "Labeling Proteins with Small Molecules by Site-Specific Posttranslational Modification," *J. Am Chem Soc.*, 2004, 126, 7754-7755.

Yin et al., "Single-Cell FRET Imaging of Transferrin Receptor Trafficking Dynamics by Sfp-Catalyzed Site-Specific Protein Labeling," *Chem. Biol.*, 2005, 12, 199-1006.

Zhyvoloup et al., "Molecular Cloning of CoA Synthase," *Biol. Chem*, 2002, 277(25), 22107-22110.

* cited by examiner

METHODS FOR GENERATING ANALOGS OF COENZYME A

CROSS REFERENCE TO RELATED APPLICATION

This application claims the benefit of U.S. Provisional Application Ser. No. 60/698,333, filed Jul. 11, 2005, which is incorporated herein by reference in its entirety.

STATEMENT OF U.S. GOVERNMENT SUPPORT

This invention was made by government support by Grant No. MCB0347681 from the National Science Foundation and Grant No. RO1GM075797 from the National Institutes of Health. The Government has certain rights in this invention.

FIELD OF THE INVENTION

This invention relates generally to the field of cell biology. Methods to covalently label proteins in vitro and in vivo by way of labeled coenzyme precursors are disclosed.

BACKGROUND OF THE INVENTION

Various publications, including patents, published applications, technical articles and scholarly articles are cited throughout the specification. These cited publications are incorporated by reference herein, in its entirety and for all that they illustrate.

Selective chemical control of biochemical processes within a living cell enables the study and modification of natural biological systems in ways that may not be obtained through in vitro experiments (Cook et al., *C.R. Bioorg. Med. Chem.* 10: 829, 2002; Chen et al., *Curr Opin Biotechnol.* 16:35, 2005). Accordingly, access to promiscuous metabolic pathways has provided a unique chemical entry into small molecule engineering in vivo (Mahal et al, *C.R. Science* 276: 1125, 1997). A method for covalent reporter labeling of carrier proteins using promiscuous phosphopantetheinyltransferase (PPTase) enzymes and reporter-labeled coenzyme A (CoA) has recently been described (La Clair et al., *M.D. Chem Biol.* 11:195, 2004). Until now, this method has been limited to in vitro and cell-surface protein labeling, as CoA derivatives have not been shown to penetrate the cell (La Clair et al., *M.D. Chem Biol.* 11:195, 2004; Mercer et al., *Chem Bio Chem* 2005; George et al., *Am. Chem Soc.,* 126:8896, 2004; Yin et al., *Am Chem Soc.* 126:13570, 2004; Yin et al., *Am Chem Soc.* 126:7754, 2004). To overcome this obstacle, labeled metabolic precursors may be delivered to the cell culture, which results in cellular uptake and metabolic conversion into active, labeled CoA derivatives. In the process, a chemoenzymatic route to protein modification via a four-step sequence is established.

The chemical synthesis and activity of CoA has been studied for well over a century, yet the full biosynthesis of the cofactor has only recently been elucidated in prokaryotes and eukaryotes (Mishra et al., *Chem Rev.,* 100:3283, 2000, Mishra et al., *Bacteriol.,* 183:2774, 2001; Martin et al., *Biochem. Biophys. Res. Commun.* 192:1155, 1993; Strauss et al., *Biol. Chem.* 276:13513, 2001; Daugherty, et al., *Biol. Chem.* 277: 21431, 2002; Kupke et al., *Biol. Chem.* 278:38229, 2003; Zhyvoloup et al., *Biol. Chem* 277:22107, 2002 and Worrall et al., *Biochem.* 215:153, 1983). CoA is biosynthesized from vitamin B5 by five enzymes in *E. coli*, CoaA-CoaE, while eukaryotes contain a fusion of CoaD and CoaE, PPAT/DPCK. Knowledge of the substrate specificity of these enzymes remains incomplete, although some evidence points to promiscuity within this pathway. Early studies on CoaA indicated that the enzyme will also accept pantetheine as a substrate (Abiko, *Biochem* 61:290, 1967 and Shimizu et al., *Biol. Chem* 37:2863, 1973). This ability has since been used in the chemoenzymatic synthesis of CoA analogs (Rudik et al., *Biochemistry* 39:92, 2000; Martin et al., *J. Am. Chem. Soc.,* 116:4660, 1994; Schwartz et al., *Biochemistry* 34:15459, 1995 and Nazi et al., *Anal. Biochem.,* 324:100, 2004). This permissiveness suggests the ability of the CoA biosynthetic pathway to convert reporter-labeled pantetheine to reporter-labeled CoA in vivo. To this end, the synthesis of fluorescently-labeled pantetheine analogs provides a direct link to reporter-labeled post-translational modifications (Mandel, A L et al. 2004).

SUMMARY OF THE INVENTION

The present invention features methods to generate analogs of coenzyme A in vitro and in a cell. In one aspect of the invention, coenzyme A analogs are generated by reacting pantetheine or a derivative thereof with a reporter to form labeled pantetheine or a derivative thereof, phosphorylating the labeled pantetheine or derivative thereof to form phosphopantetheine or a derivative thereof, adenylating the labeled phosphopantetheine or derivative thereof to form a labeled dephosphoCoenzyme A or derivative thereof, and phosphorylating the 3'-hydroxyl of the labeled dephosphoCoenzyme A or derivative thereof to form a labeled coenzyme A analog or derivative thereof.

In a detailed embodiment, the pantetheine or derivative thereof comprises three modules, a ω-functionalized amine, sidechain, an α-aminoacid, or β-aminoacid, or linker, and a modulator. The ω-functionalized amine, sidechain, α-aminoacid β-aminoacid, linker, or modulator may comprise a reporter. In a further aspect, pantetheine or an analog thereof, can be synthesized by microwave-assisted nucleophilic ring opening of pantolactone, and may further comprise a reporter. The reporter can be an affinity reporter, colored reporter, fluorescent reporter, magnetic reporter, radioisotopic reporter, peptide reporter, metal reporter, nucleic acid reporter, lipid reporter, glycosylation reporter, reactive reporter, enzyme inhibitor, biomolecular substrate, and the like, or a precursor to any of such reporters.

In a further detailed embodiment, the steps of the inventive method are enzyme-catalyzed. Phosphorylation of the labeled pantetheine or derivative thereof can be catalyzed by a kinase such as pantothenate kinase. Adenylation of the labeled phosphopantetheine or derivative thereof can be catalyzed by an adenylyltransferase such as phosphopantetheine adenylyltransferase. Phosphorylation of the 3'-hydroxyl of the labeled dephosphoCoenzyme A or derivative thereof can be catalyzed by dephospho-CoA kinase.

In a still further detailed embodiment, the method to generate analogs of coenzyme A further comprises reacting the labeled coenzyme A analog or derivative thereof with a carrier protein domain to form a labeled protein. The carrier protein domain comprises a fusion construct between a peptide or carrier protein domain and a protein of interest. This reaction can be catalyzed by an enzyme such as those in the class of phosphotransferases. An example of such a phosphotransferase compatible with the methods of the present invention is 4'-phosphopantetheinyltransferase.

Another aspect of the present invention features methods to generate coenzyme A analogs in a cell. Such coenzyme A analogs are generated by reacting pantetheine or a derivative thereof with a reporter to form labeled pantetheine or a derivative thereof, contacting the cell with the labeled pantetheine or derivative thereof such that the labeled pantetheine or derivative thereof enters the cell, phosphorylating the labeled pantetheine or derivative thereof to form phosphopantetheine or a derivative thereof, adenylating the labeled phosphopantetheine or derivative thereof to form a labeled dephosphoCoenzyme A or derivative thereof, and phosphorylating the 3'-hydroxyl of the labeled dephosphoCoenzyme A or derivative thereof to form a labeled coenzyme A analog or derivative thereof.

In a detailed embodiment, the cell is a eukaryote, prokaryote, or archaebacterial cell.

In a further detailed embodiment, the pantetheine or derivative thereof comprises three modules, a ω-functionalized amine, sidechain, an α-aminoacid, or β-aminoacid, or linker, and a modulator. The ω-functionalized amine, sidechain, α-aminoacid β-aminoacid, linker, or modulator may comprise a reporter. The reporter can be an affinity reporter, colored reporter, fluorescent reporter, magnetic reporter, radioisotopic reporter, peptide reporter, metal reporter, nucleic acid reporter, lipid reporter, glycosylation reporter, reactive reporter, enzyme inhibitor, biomolecular substrate, and the like, or a precursor to any of such reporters.

In a further detailed embodiment, the steps of the inventive method are enzyme-catalyzed. Phosphorylation of the labeled pantetheine or derivative thereof can be catalyzed by a kinase such as pantothenate kinase. Adenylation of the labeled phosphopantetheine or derivative thereof can be catalyzed by an adenylyltransferase such as phosphopantetheine adenylyltransferase. Phosphorylation of the 3'-hydroxyl of the labeled dephosphoCoenzyme A or derivative thereof can be catalyzed by dephospho-CoA kinase.

The methods of the present invention find wide application in characterizing biochemical pathways as well as characterizing protein expression, activity, or function in a cell. Accordingly, the analogs generated by the methods of the invention may be used to identify proteins, isolate proteins, assay for the expression and/or activity of proteins, screen for proteins, quantify temporal events related to the expression of proteins, assay for the function of proteins, detect the location of proteins within a cell, inhibit proteins, activate proteins, examine the structure of proteins, assay for regulation of proteins, identify a cell, cell line, organism, or class of organisms based on the presence or absence of a protein, or determine the virulence level of a cell or organism. The analogs that may be used for these purposes include without limitation, the labeled pantetheine or derivatives thereof, the phosphopantetheine analogs and derivatives thereof, the labeled dephosphoCoenzyme A analogs and derivatives thereof, and the labeled coenzyme A analogs and derivatives thereof.

DETAILED DESCRIPTION OF ILLUSTRATIVE EMBODIMENTS

Various terms relating to the methods and other aspects of the present invention are used throughout the specification and claims. Such terms are intended to be construed according to their ordinary meaning in the art.

Figure 1:
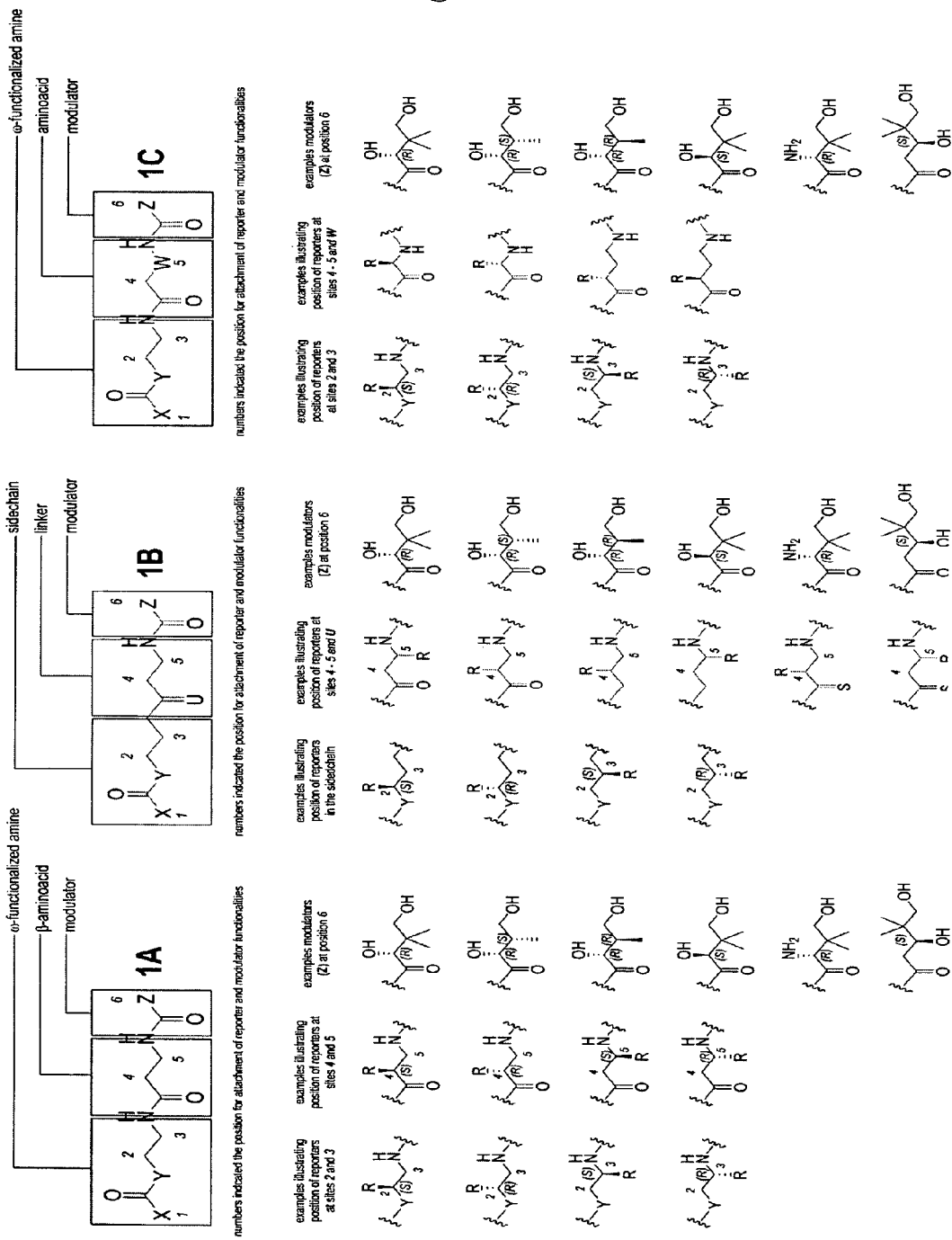
FIG. 1 shows the structure of the pantetheine analogs (1A-1C) with representation of exemplary modules.

"Coenzyme" refers to a catalytically active, low molecular mass component of an enzyme; and also refers to a dissociable, low-molecular mass active group of an enzyme that transfers chemical groups or hydrogen or electrons. Coenzyme A (CoA) is an exemplary coenzyme. Non-natural coenzyme derivatives, for example, non-natural coenzyme A derivatives, can be synthesized to contain modifications of the natural CoA molecule with variant moieties at key locations on the molecule. For instance, a library of derivatized functionality at backbone carbons within the modulator, α-aminoacid or β-aminoacid or linker and ω-functionalized amine or sidechain sub-groups of pantetheine can be created. These derivatives can contain variation within the functionality within the pantetheine backbone as given by a reporter (R) as shown in FIG. 1. Modifications about the reporter R can include the appendage of alkyl, alkoxy, aryl, aryloxy, hydroxy, halo, thiol groups or be an antigen, dye, chromaphore, cofactor, peptide, ketide, polyketol, terpene, ligand, polymer, surface, oligonucleotide, initiator, radiolabel, natural product, biosynthetic intermediates, inhibitor, organometallic complex, photoaffinity reporter.

FIG. 1 shows the structure of the pantetheine analogs (1A-1C) with representation of exemplary modules. Pantetheine is constructed of three modules. The first module contains an ω-functionalized amine or a sidechain. The second module contains either α-aminoacid, linker or β-aminoacid. The third module contains a modulator. X can be but is not limited to alkyl chain, reporter (R), cofactor, peptide, ketide, polyketol, terpene, ligand, polymer, site for surface attachment, initiator, oligonucleotide, radiolabel, natural product, biosynthetic intermediates, inhibitor, or organometallic complex. U can but is not limited to an oxygen, sulfur or two hydrogens. Y can be but is not limited to N, O, S or P atom or a methylene group, $CH_2$. W can be but is not limited to an aromatic, alkyl, polyether, polymer, or alkenyl chain.

"Carrier protein domain" refers to a protein sequence obtained from a biosynthetic gene that naturally is modified by CoA or a CoA derivative by a phosphopantetheinyl transferase (PPTase). This domain can either be a full protein, a complex of proteins, a fusion construct, or a short peptide sequence which may be derived from natural biosynthetic genes or synthesized artificially. Artificial synthetic peptide substrates can be carrier protein domains including, but are not limited to, the 11-residue ybbr tag. Yin et al., *Proc. Natl. Acad. Sci. U.S.A.* 102:15815, 2005. Artificial synthetic peptide substrates and derivatives thereof can be used as a protein fusion or as the peptide substrate not fused to another peptide.

The carrier protein domain can be labeled with the reporter that is catalytically transferred from the coenzyme, for example, coenzyme A.

"Apo-synthase" or "apo-carrier protein" refers to a synthase containing a carrier protein, a carrier protein or a peptide portion of a carrier protein that contains a serine residue that can be 4'-phosphopantetheinylated, but is not 4'-phosphopantetheinylated. The term "hapo-" denotes a state of protein modification.

"Holo synthase" or "holo-carrier protein" refers to a synthase containing a carrier protein, a carrier protein or a peptide portion of a carrier protein that contains a serine residue that has been 4'-phosphopantetheinylated by natural Coenzyme A. The term "holo-" denotes a state of protein modification.

"Crypto-synthase" or "crypto-carrier protein" refers to a synthase containing a carrier protein, a carrier protein or a peptide portion of a carrier protein that contains a serine residue that has been 4'-phosphopantetheinylated by a modified derivative of Coenzyme A bearing a reporter. The term "crypto-" denotes a state of protein modification.

"Carrier protein-enzyme-coenzyme complex" refers to derivatives of coenzyme A labeled with a reporter that transfer the reporter and selectively mark a carrier protein domain. The attachment of the reporter provides a device for selection, identification and/or recognition of the biosynthetic enzyme. This process arises through the formation of an enzyme-coenzyme complex. Formation of this complex can occur prior to or after the formation of a complex between the enzyme and its carrier protein substrate. The enzyme-coenzyme complex and/or carrier protein-enzyme-coenzyme complex is modified by the appendage of a reporter.

"Target" refers to a molecule that has an affinity for a given reporter. Targets may be naturally occurring or man-made molecules. Also, they can be employed in their unaltered state or as aggregates with other species. Targets can be attached, covalently or noncovalently, to a binding member, either directly or via a specific binding substance. Examples of targets that can be employed in accordance with this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-reporters. As the term target is used herein, no difference in meaning is intended. Typically, a "reporter-target pair" is formed when two macromolecules have combined through molecular recognition to form a complex.

"Library" refers to a collection of individual analogs of coenzymes or reporters. Specificity of individual units of coenzymes and reporters allows identification of specific biosynthetic enzymes within a solution, complex mixture or cell extract.

"Fused construct" refers to known CP domains having a consensus sequence within which the post-translational modification takes place. A fusion protein of the present invention can contain the consensus amino acid sequence or a homologous sequence thereof. The fusion partner can be as short as 13 amino acids, but it is considered a phosphopantetheinylation site if it has the consensus pattern. The consensus sequence is the following: [DEQGSTALMKRH]-[LIVMFYSTAC]-[GNQ]-[LIVMFYAG]-[DNEKHS]-S-[LIVMST]-{PCFY}-[STAGCPQLIVMF]-[LIVMATN]-[DENQGTAKRHLM]-[LIVMWSTA]-[LIVGSTACRj-x(2)-[LIVMFA]; wherein S is the pantetheine attachment site.

*Concise Encyclopedia Biochemistry*, Second Edition, Walter de Gruyter, Berlin New-York (1988); Pugh E. L., et al., *J, Biol. Chem.* 240:4727, 1965; Witkowski et al. *Eur. J. Biochem.* 198:571, 1991; http://us.expasy.org/cgi-bin/nicedoc.pl7PDOC00012.

The pattern rules are as follows. The PA (pattern) lines contains the definition of a PROSITE pattern. The patterns are described using the following conventions: The standard IUPAC one-letter codes for the amino acids are used. The symbol V is used for a position where amino acid substitiutions is accepted. Ambiguities are indicated by listing the acceptable amino acids for a given position, between square parentheses '[ ]'. For example: [ALT] stands for Ala or Leu or Thr. Ambiguities are also indicated by listing between a pair of curly brackets '{ }' the amino acids that are not accepted at a given position. For example: {AM} stands for any amino acid except Ala and Met. Each element in a pattern is separated from its neighbor by a '-'. Repetition of an element of the pattern can be indicated by following that element with a numerical value or a numerical range between parenthesis. For example: x(3) corresponds to x-x-x, x(2,4) corresponds to x-x or x-x-x or x-x-x-x. When a pattern is restricted to either the N- or C-terminal of a sequence, that pattern either starts with a '<' symbol or respectively ends with a '>' symbol. In some rare cases (e.g. PS00267 or PS00539), '>' can also occur inside square brackets for the C-terminal element. T-[GSTV]-P-R-L-[G>] 'means that either T-[GSTV]-P-R-L-G' or 'F-[GSTV]-P-R-L>' are considered. A period ends the pattern.

One aspect of the invention features methods generate analogs of coenzyme A, comprising reacting pantetheine or a derivative thereof with a reporter, phosphorylating the labeled pantetheine or derivative thereof to form labeled phosphopantetheine or derivative thereof pantetheine, adenylating the labeled phosphopantetheine or derivative thereof to form labeled dephosphoCoenzyme A, or a derivative thereof, phosphorylating the 3'-hydroxyl of the labeled dephosphoCoenzyme A or derivative thereof to form a labeled coenzyme analog or derivative thereof.

In a preferred embodiment, the pantetheine or derivative of pantetheine comprises three modules: (1) modulator, (2) α-aminoacid or β-aminoacid or linker and (3) ω-functionalized amine or sidechain. Examples of the ω-functionalized amine or sidechain include without limitation 3,3-dimethyl-1,2-diaminobutane, 1-phenyl-1,2-ethanediamine, 3-phenyl-1,2-propanediamine, 3-aminoalanine, 1,2-propanediamine, 1,2-butanediamine, 1-amino-2-propanol, 2-amino-1-phenylethanol, α-(aminomethyl)-benzeneethanol, propaneamine, butaneamine, hexaneamine, phenethylamine, 1-amino-3-propanol, 1-amino-3-chloropropane, 1-amino-3-bromopropane, 1,2-pentanediamine where Y=N or 1-propanol, 1-butanol, 1-hexanol, 1-phenethanol where Y=O. Examples of α-aminoacid include without limitation tryptophan, lysine, methionine, phenylalaine, threonine, valine, leucine, isoleucine, arginine, tyrosine, glycine, serine, glutamic acid, aspartic acid, taurine, histidine, proline, alanine, ornithine, aminobutyric acid, aminohexanoic acid, aminoisobutyric acid, argining, asparagine, aspartic acid, butylglycine, citrulline, cyclohexylalanine, cysteine, diaminobutanoic acid, diaminopropionic acid, glutamic acid, glutamine, homoserine, hydroxyproline, isoleucine, isonipecotic acid, methionine, norleucine, norvaline, penicillamine, phenylalanine, phenylglycine, praline, sarcosine, serine, statine, thienylalanine, threonine, tryptophan, homocitrulline, t-butylglycine, α-fluoroglycine, 3,3,3-trifluoroalanine, 2-methylalanine, α,α-diphenylglycine, isovaline, α-methylmethionine, 2-amino-2-fluoromethyl-3-(1(3)h-imidazol-4-yl)- propionic acid, 2-amino-2-(2,2-dimethyl-benzo[1,3]dioxol-5-ylmethyl)-but-3-ynoic acid, 2-amino-2-furan-2-yl-propionic acid, 2-amino-2-methyl-hex-5-enoic acid or 5-iodo-tryptophan. Examples of β-aminoacids include without limitation β-alanine, 2-hydroxy-β-alanine, 2-amino-β-alanine, 2-methyl-β-alanine, 2-ethyl-β-alanine, 2-phenyl-β-alanine, 3-hydroxy-β-alanine, 3-amino-β-alanine, 3-methyl-β-alanine, 3-ethyl-β-alanine, 3-phenyl-β-alanine, 2,2-dimethyl-β-alanine, 2,2-diphenyl-β-alanine, 3,3-dimethyl-β-alanine, 3,3-diphenyl-β-alanine, 2-isopropyl-β-alanine, 3-isopropyl-β-alanine, 2-t-butyl-β-alanine, 3-t-β-alanine, 2-fluoro-β-alanine, 3-fluoro-β-alanine, 2,2-difluoro-β-alanine, 3,3-difluoro-β-alanine, 2,2,3,3-tetrafluoro-p-alanine, β-aminoacrylic acid, 3-amino-propynoic acid, anthranilic acid, 2-amino-cyclohexanecarboxylic acid, 2-amino-cyclopentanecarboxylic acid, 2-amino-cyclopropanecarboxylic acid, 3-amino-oxetane-2-carboxylic acid, 4-amino-tetrahydro-furan-3-carboxylic acid, 4-amino-furan-3-carboxylic acid, 2-amino-3,3-dimethyl-cyclopropanecarboxylic acid, 2-amino-3,3-difluorocyclopropanecarboxylic acid, pyrrolidine-3-carboxylic acid or piperidine-3-carboxylic acid. Examples of the linker include without limitation 1-amino-3-butanone, 4-amino-3-methyl-2-butanone, 4-amino-3-ethyl-2-butanone, 4-amino-3-propyl-2-butanone, 4-amino-3-phenyl-2-butanone, 4-amino-2-pentanone, 4-amino-4-phenyl-2-butanone, 4-amino-2-hexanone or 4-amino-2-heptanone where U=oxygen, or β-alaninamide, 2-hydroxy-β-alaninamide, 2-amino-β-alaninamide, 2-methyl-β-alaninamide, 2-ethyl-β-alaninamide, 2-phenyl-β-alaninamide, 3-hydroxy-β-alaninamide, 3-amino-β-alaninamide, 3-methyl-β-alaninamide, 3-ethyl-β-alaninamide, 3-phenyl-β-alaninamide where U=oxygen; or 1-amino-3-butane, 4-amino-3-methyl-2-butane, 4-amino-3-ethyl-2-butane, 4-amino-3-propyl-2-butane, 4-amino-3-phenyl-2-butane, 4-amino-2-pentane, 4-amino-4-phenyl-2-butane, 4-amino-2-hexane, 4-amino-2-heptane, where U=H, H; or 1-amino-3-butanthione, 4-amino-3-methyl-2-butanthione, 4-amino-3-ethyl-2-butanthione, 4-amino-3-propyl-2-butanthione, 4-amino-3-phenyl-2-butanthione, 4-amino-2-pentanthione, 4-amino-4-phenyl-2-butanthione, 4-amino-2-hexanthione, 4-amino-2-heptanthione where U=S. The modulator typically contains a dihydroxy acid or aminohydroxy acid, and preferably is pantoic acid or a homolog or derivative or pantoic acid. FIG. 1 depicts the assembly of these modules.

The modulator, α-aminoacid, β-aminoacid, linker, ω-functionalized amine or sidechain can comprise a reporter. Non-limiting examples of such a reporter include Dansyl, BODIPY, fluoresceine, Texas red, carboxy-X-rhodamine, coumarin, aminocoumarin, oregon green, resorufin, rhodamine green, tetracyclin biotin, mannose, galactose, glucose, methotrexate, FK506.

The phosphorylation of the labeled pantetheine or derivative of pantetheine may be effectuated by any process suitable in the art to phosphorylate a compound. In a preferred embodiment, the phosphorylation is catalyzed by an enzyme of the enzyme class of kinases. Non-limiting examples of such kinases include, diacylglycerol kinase, ammonia kinase, beta-adrenergic-receptor kinase, branched-chain-fatty-acid kinase, butyrate kinase, D-ribulokinase, deoxynucleoside kinase, (deoxy)nucleoside-phosphate kinase, dihydrostreptomycin-6-phosphate 3'alpha-kinase, diphosphoinositol-pentakisphosphate kinase, farnesyl-diphosphate kinase, galactokinase, glucosamine kinase, glutamate 5-kinase, glutamate 1-kinase, homoserine kinase, inositol-trisphosphate 3-kinase, inositol-hexakisphosphate kinase, undecaprenol kinase, L-arabinokinase, lombricine kinase, mannokinase, myosin-heavy-chain kinase, NAD+ kinase, opheline kinase, rhodopsin kinase, pantetheine kinase, phosphatidylinositol 3-kinase, 1-phosphatidylinositol-3-phosphate 5-kinase, phosphatidylinositol-4,5-bisphosphate 3-kinase, phosphatidylinositol-4-phosphate 3-kinase, phosphoglycerate kinase, phosphoglycerate kinase (GTP), polynucleotide 5'-hydroxy-kinase, pyridoxal kinase, [pyruvate dehydrogenase (lipoamide)] kinase, selenide, water dikinase, rhodopsin kinase, shikimate kinase, taurocyamine kinase, thiamine-diphosphate kinase, xylulokinase, phosphoprotein phosphatase, protein-tyrosine-phosphatase, protein kinase (CDK/MAK), protein-tyrosine kinase, protein-tyrosine kinase (PTK, not ETK, WZC), protein-tyrosine kinase, protein-tyrosine kinase (PTK, not ETK, WZC), protein-tyrosine kinase, protein-tyrosine kinase (PTK, not ETK, WZC), protein kinase, protein-tyrosine kinase, protein-tyrosine kinase (PTK, not ETK, WZC), protein-tyrosine kinase, protein-tyrosine kinase (PTK, not ETK, WZC), protein-tyrosine kinase, protein-tyrosine kinase (PTK, not ETK, WZC), diacylglycerol kinase, alkylglycerol kinase, 1-phosphofructokinase, 2-dehydro-3-deoxygluconokinase, 5-dehydro-2-deoxygluconokinase, 5-methyldeoxycytidine-5'-phosphate kinase, S-methyl-5-thioribose kinase, 6-phosphofructo-2-kinase, glycerone kinase, acetylglutamate kinase, ceramide kinase, adenosine kinase, adenylate kinase, adenylyl-sulfate kinase, agmatine kinase, alkylglycerone kinase, allose kinase, ammonia kinase, arginine kinase, beta-glucoside kinase, branched-chain-fatty-acid kinase, [3-methyl-2-oxobutanoate dehydrogenase (lipoamide)] kinase, butyrate kinase, caldesmon kinase, carbamate kinase, protein kinase, choline kinase, creatine kinase, cytidylate kinase, D-arabinokinase, D-ribulokinase, deoxyadenosine kinase, (deoxy)adenylate kinase, deoxycytidine kinase, deoxyguanosine kinase, T2-induced deoxynucleotide kinase, thymidine kinase, dephospho-CoA kinase, sphinganine kinase, erythritol kinase, ethanolamine kinase, farnesyl-diphosphate kinase, pyruvate kinase, formate kinase, fructokinase, fucokinase, galactokinase, galacturonokinase, glucokinase, glucosamine kinase, lucuronokinase, glutamate 5-kinase, glycerate kinase, glycerol kinase, guanidinoacetate kinase, guanylate kinase, hamamelose kinase, hexokinase, homoserine kinase, hydroxyethylthiazole kinase, hydroxylysine kinase, hypotaurocyamine kinase, inosine kinase, inositol-tetrakisphosphate 5-kinase, inositol-tetrakisphosphate 1-kinase, inositol 3-kinase, undecaprenol kinase, kanamycin kinase, dehydrogluconokinase, L-arabinokinase, L-fuculokinase, L-xylulokinase, tetraacyldisaccharide 4'-kinase, lombricine kinase, mannokinase, mevalonate kinase, Ca2+/calmodulin-dependent protein kinase, acylglycerol kinase, adenylate kinase, myosin-light-chain kinase, NAD+kinase, nucleoside-diphosphate kinase, nucleoside-phosphate kinase, nucleoside-triphosphate-adenylate kinase, opheline kinase, pantothenate kinase, agmatine kinase, 1-phosphatidylinositol 4-kinase, phosphatidylinositol 3-kinase, 6-phosphofructokinase, phosphoglucokinase, phosphoglycerate kinase (GTP), phosphomethylpyrimidine kinase, phosphomevalonate kinase, phosphoribokinase, phosphoribulokinase, phosphorylase kinase, polyphosphate kinase, protamine kinase, protein-histidine pros-kinase, protein-histidine tele-kinase, protein-tyrosine kinase, protein-tyrosine kinase (PTK, not ETK, WZC), protein kinase, protein-tyrosine kinase, protein-tyrosine kinase (PTK, not ETK, WZC), protein kinase, protein kinase, pseudouridine kinase, diphosphate-purine nucleoside kinase, pyridoxal kinase, pyruvate kinase, pyruvate water dikinase, NADH kinase, rhamnulokinase, riboflavin kinase, [RNA-polymerase]-subunit kinase, [RNA-polymerase]-subunit kinase, ribosylnicotinamide kinase, scyllo-inosamine 4-kinase, sedoheptulokinase, shikimate kinase, sphinganine kinase, streptomycin 6-kinase, streptomycin 3-kinase, streptomycin 6-kinase, tagatose kinase, taurocyamine kinase, thiamine kinase, thiamine-diphosphate kinase, thiamine-phosphate kinase, thymidine kinase, dTMP kinase, dTMP kinase, triokinase, [tyrosine 3-monooxygenase] kinase, uridine kinase, xylulokinase, protein kinase (CaMK, MLCK, PhK, SNF, KIN, NIM1, MAPKAP, POLO, CHK, ULK, RSK-2nd domain). In a more preferred embodiment, the phosphorylation is catalyzed by pantothenate kinase.

The adenylation of the labeled phosphopantetheine or derivative thereof to form a labeled dephosphoCoenzyme A or derivative thereof may be effectuated by any process suitable in the art to adenylate a compound. In a preferred embodiment, the adenylation is catalyzed by an enzyme. In a more preferred embodiment, the adenylation is catalyzed be an adenylyltransferase. Non-limiting examples of adenylyltransferases include ATP adenylyltransferase, adenylylsulfate-ammonia adenylyltransferase, anthranilate adenylyltransferase, glucose-1-phosphate adenylyltransferase, [glutamate-ammonia-ligase] adenylyltransferase, nicotinamide-nucleotide adenylyltransferase, nicotinate-nucleotide adenylyltransferase, phenylalanine adenylyltransferase, ribose-5-phosphate adenylyltransferase, aldose-1-phosphate adenylyltransferase, and sulfate adenylyltransferase. In a still more preferred embodiment, the adenylyltransferase is phosphopantetheine adenylyltransferase.

Alternatively, generation of the labeled dephosphoCoenzyme A or derivative thereof may be accomplished by dephosphorylation catalyzed by the action of a phosphatase. Such a reaction was recently described by Silva et al., *Drug Metabolism Disposition* 32: 1304, 2004. Still another alternative means to generate the labeled dephosphoCoenzyme A or derivative thereof is to isomerize iso-CoA through cyclic-CoA to CoA, as described by Burns et al., *J. Biol. Chem.*, 280:16550, 2005.

The adenylation step can include modifications within the adenylation reagent, such as adenosine triphosphate, ATP, as shown in FIG. 1. Any derivative or surrogate of ATP may be used, including without limitation, precursors adenosine diphosphate, ADP, or adenosine monophosphate, AMP. This can include the use of alternate nucleotide phosphates including thymidine triphosphate, TTP, guanosine triphosphate, GTP, and cytidine triphosphate, CTP and their biosynthetic precursors. Modifications can include AMP, ADP, and ATP derivatives that bear modifications within the carbohydrate side chain, for instance 2-deoxyriboses or 2-aminoriboses or 2-fluororiboses or modifications within the adenine base including the application of adenine mimics and N- and C-functionalized adenines such as tubercidin triphosphate, 8-amino-adenosine triphosphate, 7-leazanebularin, formycin triphosphate, 5'-adenylylmethylene-diphosphonate, N-6-(benzyl)-ATP, 2-[(2-nitrophenyl)amino]ethyl triphosphate, 2-(phenylamino)ethyl triphosphate, adenosine 5'-o-(3-thio) triphosphate, 2-methylthio-AMP, 2-chloroadenosine, 2-chloro-5'-adenylylmethylenediphosphonate or other related nucleotide mimics.

The phosphorylation of the 3'-hydroxyl of the adenylated labeled dephosphoCoenzyme A or derivative thereof to form a labeled coenzyme A analog or derivative thereof may be effectuated by any process suitable in the art to phosphorylate a compound. In a preferred embodiment, the phosphorylation is catalyzed by an enzyme of the enzyme class of kinases. In a more preferred embodiment, the phosphorylation is catalyzed by dephospho-CoA kinase.

The labeled coenzyme A analog or derivative thereof may be further reacted with a carrier protein domain to form a labeled protein. The labeling reaction may be effectuated by any process suitable in the art to catalyze the transfer of the reporter to the protein. In a preferred embodiment, the labeling reaction is catalyzed by an enzyme. In a more preferred embodiment the labeling reaction is catalyzed by a phosphotransferase. In a still more preferred embodiment, the labeling reaction is catalyzed by 4'-phosphopanthetheinyltransferase.

The labeling-process may transfer a diversity of reporters, including organic or inorganic molecules, or biomolecules, or any fragment, analog, homolog, derivative, or conjugate thereof. Biomolecules include nucleic acids, polypeptides, polysaccharides, lipids, and the like. More specifically, the reporter may be, without limitation, an affinity reporter, colored reporter, fluorescent reporter, magnetic reporter, radioisotopic reporter, peptide reporter, metal reporter, nucleic acid reporter, lipid reporter, glycosylation reporter, reactive reporter, enzyme inhibitor, substrate for a biomolecule, or the like. Similarly, the reporter may be any precursor to any of the above-mentioned reporters including, but not limited to, bioorthogonal chemical labels such as ketone, azide, alkyne, or triarylphosphine analogs.

The reporter may be chosen as substrate or mimetic for study of biomolecular structure and function. For this application, the reporters function can be derived from molecules generated at the state of phosphopantetheine e using analogs such as 2A-2C, dephosphoCoA through analogs such as 3A-3C, CoA through analogs such as 4A-4C and cryptocarrier protein through analogs such as 5A-5C. This reporter can therefore be used to assist structural analyses for instance through nuclear magenetic resonance (NMR) spectroscopy, X-ray crystallographic analysis, and fluorescent methods. The reporter can also be used to guide drug design, to act as a drug or drug precursor, to act as a component of an assay. Another aspect of the present invention features methods to generate analogs of coenzyme A in a cell. Such methods comprise reacting pantetheine or a derivative thereof with a reporter, contacting the cell with the labeled pantetheine or derivative of pantetheine such that the labeled pantetheine or derivative or pantetheine enters the cell, phosphorylating the labeled pantetheine or derivative thereof to form labeled phosphopantetheine or derivative thereof pantetheine, adenylating the labeled phosphopantetheine or derivative thereof to form labeled dephosphoCoenzyme A, or a derivative thereof, phosphorylating the 3'-hydroxyl of the labeled dephosphoCoenzyme A or derivative thereof to form a labeled coenzyme analog or derivative thereof.

The cell may be any eukaryotic, prokaryotic, or archaebacterial cell. The cell may be contacted with the labeled pantetheine or derivative of pantetheine by any means suitable in the art. Numerous means to deliver small molecules to cells are known and established in the art. Non-limiting examples of such means include liposomes, microinjection, electroporation, biolistics, receptor mediated endocytosis, cell penetrating peptides, and the like. The skilled artisan will understand that delivery vehicles can vary with the cell type, and will similarly appreciate that specialized delivery vehicles and methods are available for delivery of small molecules to specific cells or tissues. In a preferred embodiment, the labeled pantetheine or derivative of pantetheine is formulated as part of the cell growth medium, and delivered to the cell by natural uptake.

The methods of the present invention may be used in a variety of applications. Non-limiting examples of such applications include preparation of fluorescent proteins in vitro and in vivo without the need to genetically engineer such proteins, as occurs with green fluorescent protein, studying biochemical processes of the cell, marking of cell signaling pathways, characterization of the cell cycle, elucidation of protein-ligand interaction, characterization of cell-cell interactions, determination of whether a cell is viable or dead, profiling cell structures, staining of cellular organelles, identification of cell type, modification of cellular function, regulation of cell differentiation, isolation of cells, profiling and identification of microbes, isolation of microbes, evaluation of embryology and developmental biology, detection of disease or disease state, evaluation of clinical samples, preparation of bioassays, protein function analysis, protein structure analysis, metabolic regulation, metabolic analysis, drug delivery, drug localization, natural product biosynthetic identification, natural product biosynthetic elucidation, natural product biosynthetic manipulation, metabolic engineering, drug screening, drug development, as a drug, and the like.

The following examples are provided to illustrate the invention in greater detail. The examples are intended to illustrate, not to limit, the invention.

EXEMPLARY EMBODIMENTS

Example 1

Pantetheine Analog Synthesis

All reactions were carried out under an atmosphere of argon in flame-dried glassware with magnetic stirring. Column chromatography was performed on 0.25 mm silica gel 60-F plates. Visualization was accomplished with UV light, o-tolidine, cerium molybdate, or ninhydrin dips followed by heating. $^1$HNMR and spectra were recorded on a 500, 400, and 300 MHz spectrometer at ambient temperature. Data were reported as follows: chemical shifts in parts per million ($\delta$, ppm) from an internal standard [deuterated methanol ($CD_3OD$), deuterated chloroform ($CDCl_3$), or deuterated dimethyl sulfoxide (DMSO)], multiplicity (s=singlet, d=doublet, t=triplet, q=quartet, and m=multiplet), integration, and coupling constant (Hz). $^{13}$CNMR were recorded on a 500, 400, and 300 MHz NMR at ambient temperature. Chemical shifts are reported in ppm from $CD_3OD$, $CDCl_3$, or DMSO. High resolution mass spectrometry was obtained using fast atom bombardment (FAB) as the ion source. The matrix in all cases was 3-nitrobenzyl alcohol and the reference was polyethylene glycol.

Synthesis of 3-{[2-(4-Methoxy-phenyl)-5,5-dimethyl-[1,3]dioxane-4-carbonyl]-amino}-propionic acid (8A1)

Pantothenic acid (7) (4.6 g, $2.24 \times 10^{-2}$ mols) was dissolved in dry DCM (30 mL). Camphor sulfonic acid (0.52 g, $2.24 \times 10^{-3}$ mols) and p-anisaldehyde-dimethoxy-acetal (3.82 mL, $2.24 \times 10^{-2}$ mols) were added to the reaction mixture. The reaction was stirred overnight at room temperature with a drying tube. The crude reaction product was concentrated and purified silica gel chromatography (6:1 hexane:EtOAC-EtOAc) to yield a white solid (8A1) (3.8 g, 51% yield). mp=135-136° C. $^1$HNMR (400 MHz, DMSO) 0.93 (s, 3H), 0.99 (s, 3H), 2.38 (t, 2H, J=6.8 Hz), 3.25 (m, 1H), 3.34 (m, 1H), 3.5.9 (d, 1H, J=10.8 Hz), 3.62 (d, H, J=10.8 Hz), 3.74 (s, 3H), 4.07 (s, 1H), 5.50 (s, 1H), 6.91 (d, 2H, J=8.8 Hz), 7.41 (d, 2H, J=8.8 Hz). $^{13}$C-NMR (400 Mz, DMSO) 19.7, 22.2, 33.2, 34.4, 34.9, 55.8, 78.0, 83.8, 101.1, 114.0, 128.4, 131.1, 160.3, 168.9, 173.8. IR (NaCl, thin film), 3420, 2959, 1729, 1654, 1617, 1540, 1520, 1251, 1105 cm$^{-1}$. MS (ESI) [M+Na]$^+$ 360.1. HRMS (FAB) (m/z): [M+H]$^+$ calcd for $C_{17}H_{23}O_6N$, 338.1598, found 338.1594.

Synthesis of 2-(4-Methoxy-phenyl)-5,5-dimethyl-[1,3]dioxane-4-carboxylic acid (2-{6-[2-(7-dimethylamino-2-oxo-2H-chromen-4-yl)-acetylamino]-hexylcarbamoyl}-ethyl)-amide (9A1)

Protected pantothenic acid 8A1 (0.434 g, $1.34 \times 10^{-3}$ mol) was dissolved in 30 mL of DMF. EDC (0.529 g, $2.68 \times 10^{-3}$ mol), HOBT (0.411 g, $2.68 \times 10^{-3}$ mol), and triethylamine (0.374 mL, $2.68 \times 10^{-3}$ mol) were added to the reaction mixture. ω-Aminoacid 6A1 (0.600 g, $1.34 \times 10^{-3}$ mol) was dissolved in 5 mL of DMF and added to the reaction mixture. The reaction stirred over night at room temperature under Ar before being evaporated to yield a yellow oil. The oil was redissolved in 50 mL of DCM and the organic layer washed with 15% citric acid (3×50 mL), saturated $NaHCO_3$ (3×50 mL), water (2×50 mL), and brine (2×50 mL) and dried with sodium sulfate. The concentrated crude product was purified by silica gel chromatography (DCM: 10% MeOH:DCM) to yield a pale yellow solid 9A1 (0.680 g, 77% yield). $^1$HNMR (400 MHz, $CDCl_3$) $\delta$ 1.04 (s, 3H), 1.06 (s, 3H), 1.21 (m, 4H), 1.39 (m, 4H), 2.38 (t, 2H, J=6.4 Hz), 3.00 (s, 6H), 3.12 (m, 4H), 3.45 (m, 2H), 3.55 (s, 2H), 3.61 (d, 1H, J=11.2 Hz), 3.66 (d, 1H, J=11.2 Hz), 3.76 (s, 3H), 4.02 (s, 1H), 5.42 (s, 1H), 6.00 (s, 1H), 6.39 (d, 1H, J=2.4 Hz), 6.48 (t, 1H, J=4.8 Hz, —NH), 6.55 (dd, 1H, J=8.8, 2.4 Hz), 6.68 (t, 1H, J=5.2 Hz, NH), 6.86 (d, 2H, J=8.8 Hz), 7.09 (t, 1H, J=6.0 Hz, NH), 7.39 (d, 2H, J=8.8 Hz), 7.46 (d, 1H, J=8.8 Hz). $^{13}$CNMR (400 Mz, $CDCl_3$) 19.4, 22.1, 26.2, 29.3, 29.5, 33.3, 35.3, 36.2, 39.2, 39.6, 40.3, 40.6, 55.5, 78.6, 84.0, 98.2, 101.5, 108.7, 109.4, 110.0, 113.9, 126.1, 127.7, 130.3, 150.8, 153.2, 156.1, 160.4, 162.3, 168.4, 169.7, 171.2. IR (NaCl, thin film), 3320, 2930, 2860, 1707, 1652, 1616, 1531, 1403 cm$^{-1}$. MS (ESI) [M+Na]$^+$687.40. HRMS (FAB) (m/z): [M+H]$^+$ calcd for $C_{36}H_{48}O_8N_4$, 665.3545, found 665.3542.

Synthesis of Labeled-Coa Analog (1A1)

Compound 9A1 (0.680 g, $1.0 \times 10^{-3}$ mol) was dissolved in 50:50 1 M HCl:THF and the reaction stirred at room temperature for 2 h. AG-1-X8 Strong Basic anionic exchange resin was added to the reaction mixture until the solution was neutral. The crude product was concentrated under vacuum and redissolved in methanol (50 mL) and washed with hexanes (3×, 20 mL). The crude product was again concentrated and purified by silica gel chromatography (DCM: 10% MeOH:DCM) to yield pure pale yellow solid 1A1 (0.529 g, 95%) with a melting point, mp=135-136° C. Compound 1A1 is an example of pantetheine analog type 1A. $^1$HNMR (400 MHz, CD3OD) $\delta$ 0.80 (s, 3H), 1.20 (m, 4H), 1.35 (m, 2H), 1.40 (m, 2H), 2.29 (t, 2H, J=6.4 Hz), 3.00 (s, 6H), 3.01 (m, 2H), 3.10 (t, 2H, J=6.8 Hz), 3.32 (m, 4H), 3.56 (s, 2H), 3.77 (s, 1H), 5.93 (s, 1H), 6.43 (d, 1H, J=2.8 Hz), 6.63 (dd, 1H, J=9.2, 2.8 Hz), 7.45 (d, 2H, J=9.2 Hz). $^{13}$CNMR (400 Mz, CDCl3) 20.9, 21.4, 27.5, 27.6, 30.2, 30.3, 36.4, 36.5, 40.3, 40.4, 40.5, 70.3, 77.1, 98.6, 109.6, 110.2, 110.4, 126.7, 152.8, 154.5, 156.9, 164.0, 170.7, 173.3, 175.7. IR (NaCl, thin film), 3488, 3310, 2917, 1712, 1634, 1606, 1542 cm-1. MS (ESI) [M+Na]+ 569.32. HRMS (FAB) (m/z): [M+H]+ calcd for C28H42O7N4, 547.3126, found 547.3121.

Example 2

In Vivo Labeling and Cellular Uptake Studies

For the in vivo carrier protein labeling studies, *E. coli* (BL-21) were transformed by electroporation with plasmids encoding the genes for VibB (*V. cholerae*) and Sfp (*B. subti*-

*lis*). Cultures were grown to $OD_{600}=0.6$ and then induced with 1 mM IPTG. At the same time differing concentrations of 7-dimethylaminocoumarinacetic acid labeled-pantetheine were added. The cultures were grown up to 16 h with time points taken at intervals to investigate uptake and labeling. The cells were centrifuged and resuspended in lysis buffer (50 mM sodium phosphate, 300 mM NaCl), washed three times in an equal volume of lysis buffer, and then lysed by incubation with lysozyme (1 mg/ml) for 1 h on ice followed by sonication. Lysates were then examined for fluorescence (excitation at 360 nm; emission at 465 nm) and run on 12% PAGE for visualization. Gels were imaged using conventional CCD imaging.

Example 3

Assessment of Effect of the Labeled-Pantetheine on E. coli Growth

To assess the effect of the labeled-pantetheine on *E. coli*, cultures of BL-21. *E. coli* were grown with increasing concentrations of the compound. Culture tubes containing 5 ml of LB were inoculated with 1 ul of *E. coli* from overnight growths. At the same time the labeled-pantetheine was added. Growth was measured by monitoring the $OD_{600}$ of the cultures over time.

Example 4

In Vitro Synthesis of Labeled-CoA and HPLC Analysis

The conversion of labeled-pantetheine to labeled-CoA was achieved in vitro by incubation of the pantetheine analogue with the enzymes CoaA, CoaD, and CoaE from *E. coli*. Reactions were run in 20 mM KCl, 5 mM ATP, 10 mM $MgCl_2$, and 50 mM Tris-Cl pH 7.5. CoaA (4 uM), CoaD (15 uM), and CoaE (30 mM) were then added and the reactions were incubated at room temperature for 1 h. Progress of the reactions was analyzed using reverse-phase C18 column equilibrated in 100% solution A (0.05% aqueous TFA). Products were eluted using a gradient with solution B (0.05% aqueous TFA) at a flow rate of 0.9 mL/min The method used began with an isocratic step from 0 to 5 min at 100% solution A, followed by an increasing gradient with solution B until at 25 min the solvent composition was 50%. Solvent A and 50% Solvent B. The in vitro synthesis reactions of labeled-CoA were also visualized by PAGE. The carrier protein VibB and PPTase Sfp were added to the reaction mix, incubated for 30 min at 37° C. and then run on 12% PAGE. Gels were documented using conventional CCD imaging.

Example 5

Tagging Heterologously Expressed Carrier Protein Domains

Fluorescent tagging with derivatives was repetitively conducted on proteins from crude cell lysate from recombinant *E. coli* BL21 cells expressing a carrier protein (i.e., VibB). Cell lysate was dialyzed to remove small molecules (<3 or <10 kDa), incubated with CoA-DYE and recombinant Sfp, and analyzed by SDS-PAGE. When viewed under irradiation, recombinant VibB is visualized as a fluorescent band that was verified with two methods. First, standard Coomasie staining showed the fluorescent band to have the proper molecular weight when compared to molecular weight markers. Second, an identical gel was electrophoretically transferred to a polyvinylidene fluoride (PVDF) membrane, and the fluorescent band was excised from the membrane. This membrane piece was subjected to N-terminal amino acid sequencing by Edman degradation. The first 10 amino acids of the returned sequence, MAIPKIASYP, mapped to the correct protein, VibB, when searched with BLAST against 1.4 million sequences in the GenBank. Broad applicability of these techniques is anticipated for validating proper folding and modification ability of recombinant PK and NRP systems.

One liter of *E. coli* BL21 (de3) cells, grown using standard methods of IPTG induced overexpression of recombinant proteins, were lysed by sonication at 0° C. in 30 ml of 0.1 M Tris-Cl pH 8.0 with 1% glycerol in the presence of 500 µL of a 10 mM phenylmethanesulfonyl fluoride (PMSF) solution in isopropanol with 50 µL of a protease inhibitor cocktail (a mixture of protease inhibitors with broad specificity for the inhibition of serine, cysteine, aspartic and metallo-proteases, and aminopeptidases containing 4-(2-aminoethyl)benzenesulfonyl fluoride (AEBSF), pepstatin A, E-64, bestatin, and sodium EDTA. After centrifugation at 4000×g for 10 min, 200 µL of this cell lysate was treated with 80 µL of the labeled-CoA solution and 1 µL (30 µg) of 30 mg/mL purified Sfp, and the reaction was incubated at room temperature for 30 min in darkness. An 800 µL aliquot of a 10% trichloroacetic acid solution was added and cooled at −20° C. for 30-60 min. The samples are centrifuged for 4 min, and the supernatant was removed. The pellets are resuspended in 1:1 mixture of 1.0 M Tris-HCl pH 6.8 and 2×SDS-PAGE sample buffer (100 mM Tris-Cl pH 6.8, 4% SDS, 20% glycerol, 0.02% bromophenol blue). This solution is placed in boiling water for 5-10 min and separated using SDS-PAGE electrophoresis on a 12% Tris-Glycine. Tagged proteins are visualized by trans-illumination and the resulting images captured with CCD camera. The fluorescent bands originate from cryptosynthases.

Example 6

Tagging of Purified Recombinant Carrier Protein Domains

Fluorescently-labeled CoA were prepared by selective modification of the free thiol of coenzyme A. This labeled-CoA derivative was then incubated with heterologously expressed and purified Sfp and VibB, a small protein from the *Vibrio cholera* vibriobactin biosynthetic machinery containing only one carrier protein domain. Analysis was performed with SDS-PAGE, and a single fluorescent band was visualized by eye using the appropriate wavelength of light for excitation. The excitation wavelength was chosen based on using the appropriate combination of excitation with UV-visible light and the appropriate cutoff filters. Coomasie staining of the gel verified the fluorescent reporter to be crypto-VibB.

This example demonstrates the utility of this method to fluorescently tag purified over-expressed and purified VibB, a standalone CP domain. In this example, VibB, a 32.6 kDa protein, is fluorescently-tagged. Tagging was conducted by the addition of a biotin-tagged derivative and a PPTase such as Sfp. SDS-page electrophoresis was used to separate proteins.

Recombinant His-tagged VibB, purified by nickel chromatography, was dialysed to a 0.6 mg/ml solution in 0.1M TRIS-HCl pH 8.4 with 1% glycerol. A 200 µL aliquot of this solution is treated with 80 µL of the labeled-CoA solution (see Preparation of modified CoA derivatives). The reaction is incubated at room temperature for 30 min in darkness. A 50

μL aliquot of a 10 mg/mL solution of bovine serum albumin (BSA) is added, and the protein is precipitated by the addition 800 μL of a 10% trichloroacetic acid solution and cooling at −20° C. for 30-60 min. The samples are centrifuged at 13,000×g for 4 min, and the supernatant is removed. The pellet was resuspended in 1:1 mixture of 1.0 M Tris-HCl pH 6.8 and 2×SDS-PAGE sample buffer (100 mM Tris-Cl pH 6.8, 4% SDS, 20% glycerol, 0.02% bromophenol blue). This solution was placed in boiling water for 5-10 min and separated using SDS-PAGE electrophoresis on a 12% Tris-Glycine. Tagged proteins were visualized by trans-illumination and the resulting images captured with CCD camera.

Example 7

Tagging of Natively Expressed Carrier Protein Domains

Figure 2:
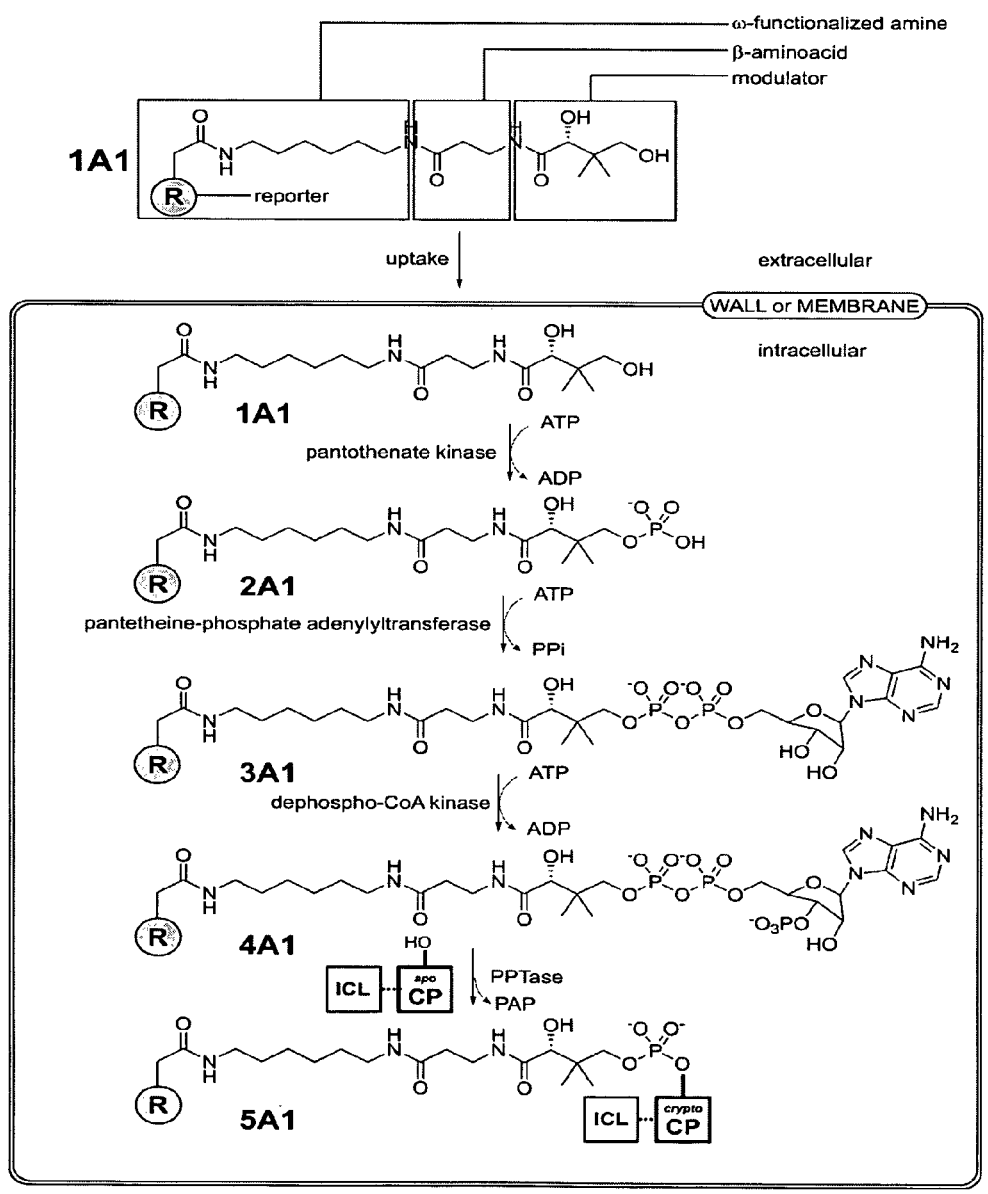
FIG. 2 shows in vivo metabolic labeling of a carrier protein (CP) via cellular uptake of an exemplary pantetheine analog (1A1) and conversion to CoA analog (4) by CoaA, CoaD, and CoaE.

Fluorescent tagging was repeated on proteins from crude cell lysate from recombinant *E. coli* K12 cells following iron-starving conditions, which include growth in minimal nutrient-media and iron chelation by growth in minimal media and addition of 2,2-dipyridyl. Reagents used for this fluorescent tagging are shown in FIG. 2. These conditions induce enterobactin production in the organism, which is synthesized by NRP synthase proteins EntB, EntE, and EntF. Both EntB and EntF contain carrier protein domains that can be post-translationally modified by 4'-phosphopantetheinyltransferase. Cell lysate from the iron starved cells was dialyzed to remove small molecules (<10 kDa), incubated with CoA-DYE and recombinant Sfp, and analyzed by SDS-PAGE. When viewed under irradiation, recombinant EntF and EntB are visualized as fluorescent bands that can be verified with two methods. First, standard Coomasie staining showed the fluorescent bands to have the proper molecular weight when compared to molecular weight markers. Second, bands from an unstained gel were subjected to mass spectroscopic protein sequencing (Qstar MS-MS) to reveal the sequences of EntF and EntB after searching GenBank protein databank.

FIG. 2 shows in vivo metabolic labeling of a carrier protein (CP) via cellular uptake of an exemplary pantetheine analog (1A1) and conversion to CoA analog (4) by CoaA, CoaD, and CoaE. This process is followed by reaction of a PPTase with (4) and a carrier protein yielding labeled protein (5). This example depicts VibB, a natural fusion construct comprised of a carrier protein fused to an isochorismate lyase (ICL). The gray circle denotes a reporter.

Figure 3:
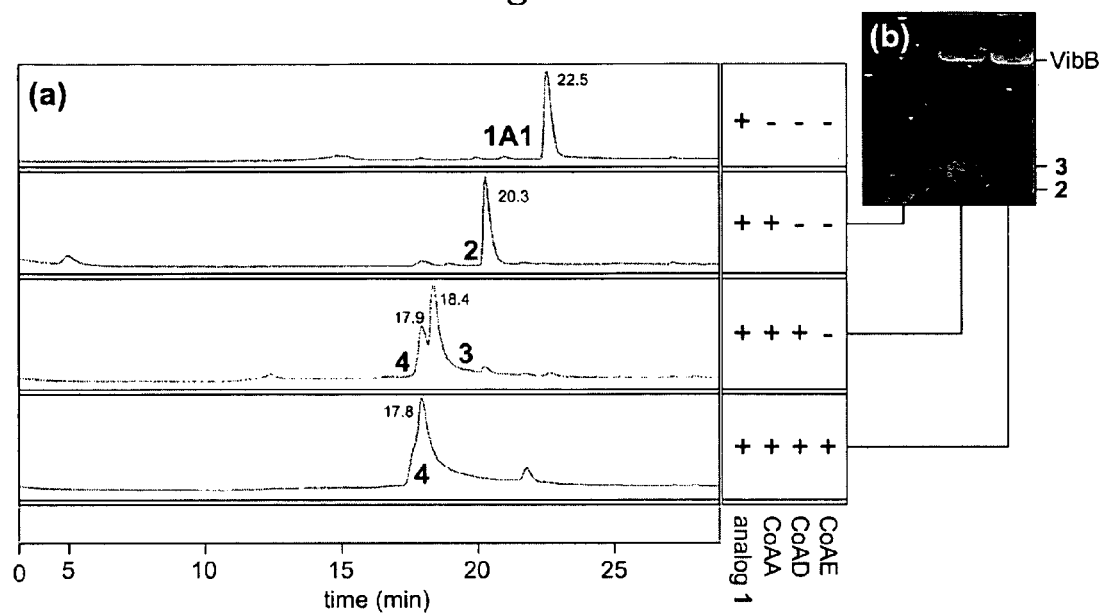
FIGS. 3a and 3b shows in vitro enzymatic reconstitution of the metabolic-labeling process.

FIG. 3 shows in vitro enzymatic reconstitution of the metabolic-labeling process. (a) HPLC analysis of the stepwise conversion of (1A1) to reporter-labeled CoA analog (4). (b) SDS-PAGE gel depicting the labeling of a carrier protein was used, by 4 with PPTase. For this example, the carrier protein was VibB, a protein in the vibriobactin synthase from *Vibriobacter cholerae*, and the PPTase was Sfp, surfactin PPTase from *Bacillus subtilis*. A fluorescent reporter was used, and the labeled carrier protein, VibB, was detected by fluorescence imaging. Intermediates (2) and (3) can also be visualized through gel analysis.

Figure 4:
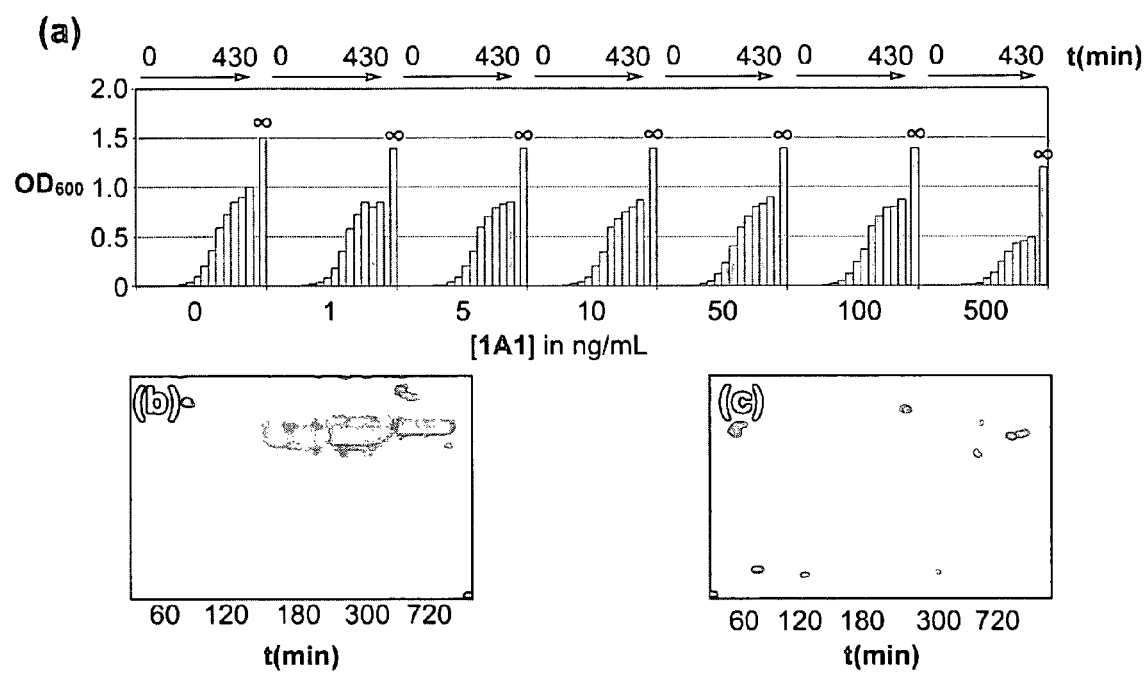
FIGS. 4a, 4b and 4c shows in vivo tagging of carrier protein fusion construct within *E. coli*.

FIG. 4 shows in vivo tagging of carrier protein fusion construct within *E. coli*. (a) Growth of *E. coli* culture (OD600) over a range in concentrations of (1A1). (b) In vivo formation of crypto-CP state following a time course after addition of 1 mM (1A1) to culture. (c) In vivo formation of crypto-CP state following a time course following addition of 100 μM (1) to culture.

Figure 5:
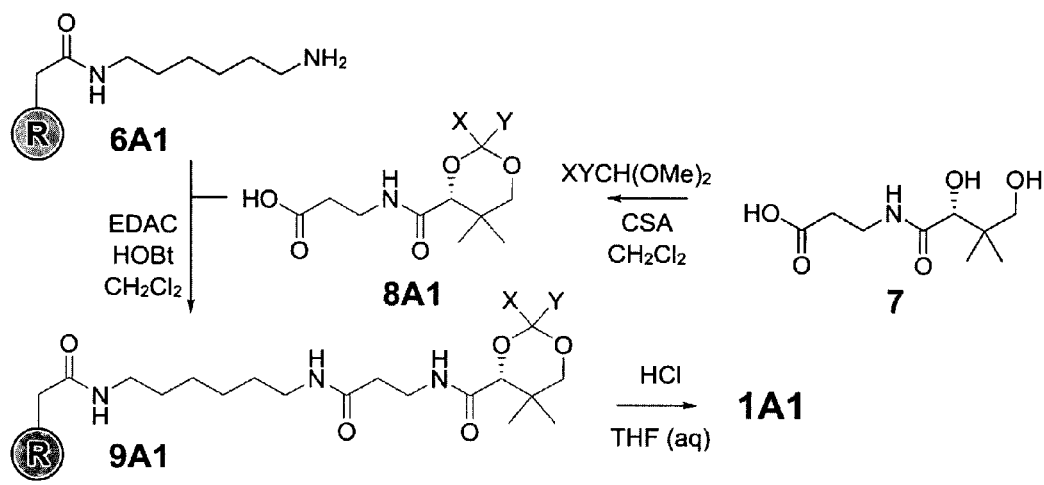
FIG. 5 shows schematic demonstrating synthesis of a pantetheine analog (1A1).

FIG. 5 shows schematic demonstrating synthesis of a pantetheine analog (1A1).

Figure 6:
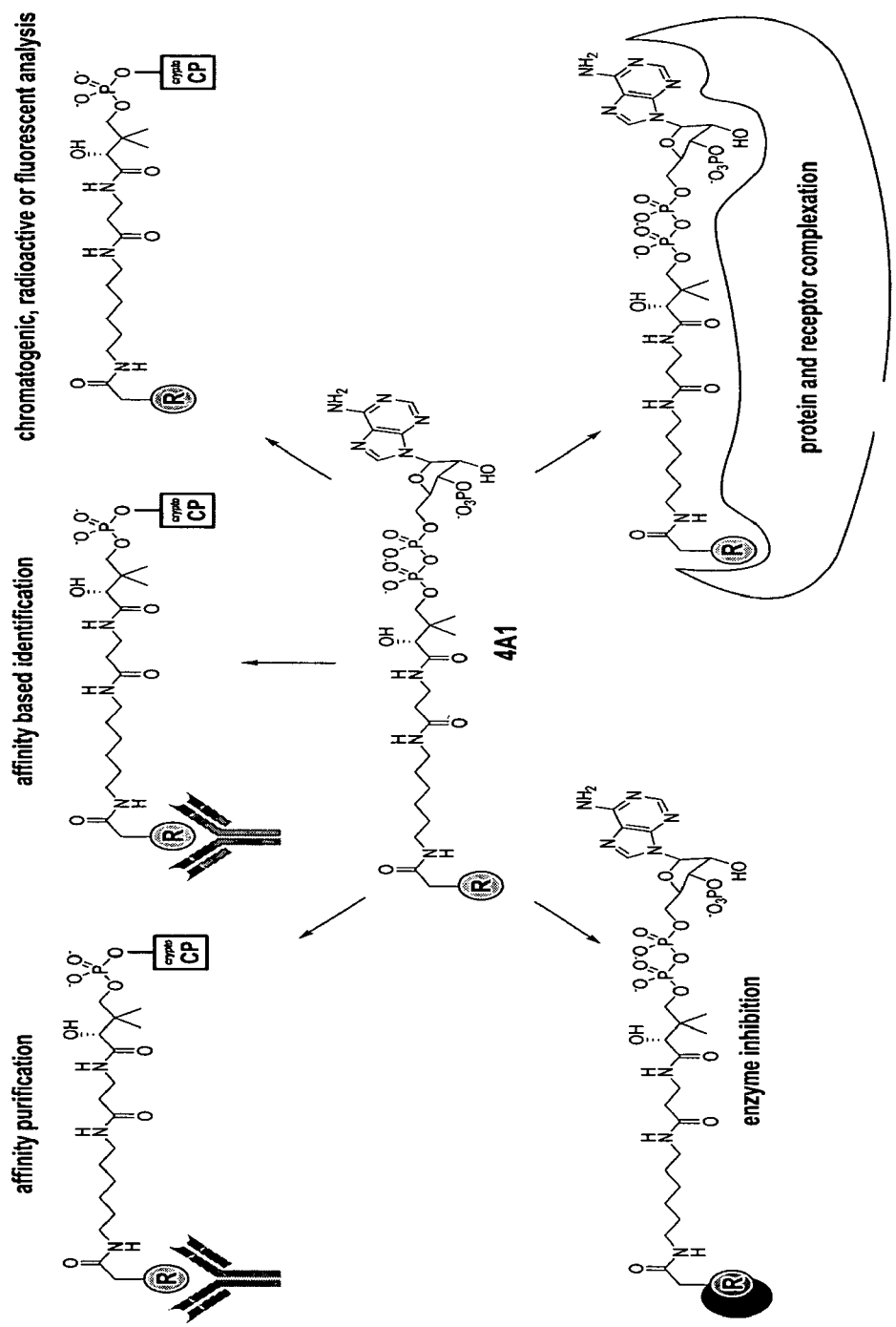
FIG. 6 shows an application of labeled CoA analogs (1A1C).

FIG. 6 shows an application of labeled CoA analogs (1A-1C). These analogs can either be used directly for biomolecular identification, analysis, or screening or they can be conjugated to a carrier protein (CP) and then be used to biomolecular identification, analysis, or screening. A combination of any of these and related methods can be developed from 1A1C.

*E. coli* K12 cells are starved of iron as follows. *E. coli* K12 cells in a 1 liter of Lauria-Bertani (LB) media was incubated at 37° C. to an OD of −0.7. The cells are treated with 2,2-dipyridyl to a final concentration of 0.2 mM and allowed to incubate an additional 4 h at 37° C. The culture was then centrifuged, and the resuspended cell pellets were lysed by sonication at 0° C. in 30 ml of 0.1 M Tris-Cl pH 8.0 with 1% glycerol in the presence of 500 μL of a 10 mM phenylmethanesulfonyl fluoride (PMSF) solution in isopropanol with 50 μL of a protease inhibitor cocktail: a mixture of protease inhibitors with broad specificity for the inhibition of serine, cysteine, aspartic and metallo-proteases, and aminopeptidases, including 4-(2-aminoethyl)benzenesulfonyl fluoride (AEBSF), pepstatin A, E-64, bestatin, and sodium EDTA, Sigma-Aldrich Inc.) An 80 μL aliquot of the modified-CoA solution was added to 200 μL of the cell lysate along with 30 ug of 30 mg/mL purified Sfp. The resulting mixture was incubated at room temperature for 30 min in darkness. Proteins were precipitated from this solution by the addition of 800 μL of a 10% trichloroacetic acid solution and cooling at −20° C. for 30-60 min. The samples were centrifuged at 4000×g for 4 min, and the supernatant is removed. The pellet was resuspended in 1:1 mixture of 1.0 M Tris-HCl pH 6.8 and 2×SDS-PAGE sample buffer (100 mM Tris-Cl pH 6.8, 4% SDS, 20% glycerol, 0.02% bromophenol blue). This solution was placed in boiling water for 5-10 min and separated using SDS-PAGE electrophoresis on a 12% Tris-Glycine. Tagged proteins were visualized by trans-illumination and the resulting images captured with CCD camera. Blotting analysis was conducted using the biotinylated-CoA derivative as described below.

Use of this method to identify proteins containing at least one CP domain within the cell lysate of native producer organism has been completed as another example. In this example, EntB, a 32.6 kDa protein, was selectively tagged within the culture of its natural host (*E. coli*). SDS-page electrophoresis was used to separate proteins. Tagging was conducted by the addition of a fluorescently-tagged derivative as given by a PPTase such as the *Bacillus subtilis* Sfp transferase. Fluorescent tagging was identified as a fluorescent band using conventional CCD image analysis.

Example 8

SDS-Page Electrophoresis

SDS-page electrophoresis was used to detect polyketide, non-ribosomal peptide, and fatty acid synthases continuing carrier proteins through protein tagging with CoA-labeled by a fluorescent dye, biotin, a carbohydrate or oligosaccharide, a peptide sequence, or another selectable moiety. Proteins from natural or engineered organisms were tagged with the use of a 4'-phosphopantetheinyltransferase and the CoA derivative, and subsequently separated by SDS-PAGE. The separated proteins were visible in the gel at this stage (as in the case of fluorescent tagging), or the gel can be further processed to allow visualization of the tagged proteins. Visualized pieces of the gel can be excised for protease digestion and analysis, protein sequencing via Edman degradation or mass spectrophotometric techniques, or extracted for solution-phase assays of the purified proteins. The whole gel can also be subjected to electrophoretic transfer of the proteins to a membrane or other substrate for blot analysis.

Example 9

Native Protein Polyacrylamide Gel Electrophoresis

This technique was used to detect PK, NRP, and fatty acid synthases continuing carrier proteins via native protein gel electrophoresis through protein tagging with CoA-labeled by a fluorescent dye, biotin, a carbohydrate or oligosaccharide, a peptide sequence, or another selectable moiety. Proteins from natural or engineered organisms were tagged with the use of a 4'-phosphopantetheinyltransferase and the CoA derivative, and subsequently separated by a native protein polyacrylamide gel. The separated proteins were visible in the gel at this stage (as in the case of fluorescent tagging), or the gel can be further processed to allow visualization of the tagged proteins. Visualized pieces of the gel can be excised for protease digestion and analysis, protein sequencing via Edman degradation or mass spectrophotometric techniques, or extracted for solution-phase assays of the purified proteins. The whole gel can also be subjected to electrophoretic transfer of the proteins to a membrane or other substrate for blot analysis.

Example 10

Blot Analysis

Blotting was performed to identify proteins with carrier protein domains. It was found that PPTases such as Sfp would accept a variety of CoA derivatives for transfer onto a carrier protein, including a biotin tag, which could be visualized by electroblotting onto nitrocellulose followed by binding with streptavidin that is modified for visualization. Biotin-CoA derivative was synthesized using a variety of linked biotin tags using a method comparable to that to attach reporters. The biotin-linked 4'-phosphopantetheine was successfully transferred to apo-VibB with recombinant Sfp. The biotin-tagged VibB was then identified by a blot: purified with SDS-PAGE or native protein gel, electro-transferred to nitrocellulose, and incubated sequentially with streptavidin-linked alkaline phosphatase and 5-bromo-4-chloro-3-indolyl phosphate/nitro blue tetrazolium (BCIP/NBT). The biotin-labeled VibB protein on the nitrocellulose membrane stained dark blue due to enzymatic dephosphorylation of BICP and precipitation of the dark blue product through oxidation by NBT. This assay provides convincing evidence that a biotin-streptavidin technique can also be used to purify PK and NRP synthases that contain carrier protein domains with affinity chromatography. This assay can be conducted with any affinity tag and molecular binding partner, including mannose-concanavalin A and peptide-antibody interactions. These results have been reproduced using mannose-linked CoA tagging to VibB with Sfp, separating on SDS-PAGE, blotting to nitrocellulose, and visualizing with concanavalin-linked peroxidase and peroxidase substrate (3-Amino-9-ethylcarbazole).

One liter of E. coli BL21 (DE3) cells induced to express recombinant VibB protein were lysed in 30 mL 1M Tris-Cl pH 8.0 with 1% glycerol in the presence of 500 µL of a 10 mM phenylmethanesulfonyl fluoride (PMSF) solution in isopropanol by sonication. A 50 µL of a protease inhibitor cocktail mixture containing protease inhibitors with broad specificity for the inhibition of serine, cysteine, aspartic and metalloproteases, and aminopeptidases including 4-(2-aminoethyl) benzenesulfonyl fluoride (AEBSF), pepstatin A, E-64, bestatin, and sodium EDTA was added to this sample prior to lysis. A 40 µL of the biotinylated-CoA analog solution was added to 200 µL of cell lysate containing overexpressed VibB and 1 µL of a 34 mg/mL solution of purified Sfp and the reaction was incubated at room temperature for 30 min in darkness.

Proteins were precipitated from this solution by the addition of 800 µL of a 10% trichloroacetic acid solution and cooling at −20° C. for 30-60 min. The samples were centrifuged at 14000×g for 4 min, and the supernatant was removed. The pellet was resuspended in 1:1 mixture of 1.0 M Tris-HCl pH 6.8 and 2×SDS-PAGE sample buffer (100 mM Tris-Cl pH 6.8, 4% SDS, 20% glycerol, 0.02% bromophenol blue). This solution was placed in boiling water for 5-10 min and separated using SDS-PAGE electrophoresis on a 12% Tris-Glycine. Following separation, the gel was transferred to nitrocellulose and blotted.

Blots were incubated with 5% milk in TBST for 30 min at room temperature with shaking. The blots were then transferred directly to 1 mL of a 5% milk in TBST solution containing 1 µL of 25 mg/mL streptavidin-alkaline phosphatase conjugate and incubated at room temperature for 1 hour. After this incubation, the blot was washed 3 times for 10 min with 20 mL of TBST at room temperature. Finally, the blot was incubated in 2 mL of Alkaline-phosphatase substrate solution (0.15 mg/mL EOT, 0.30 mg/mL NBT, 100 mM Tris, 5 mM $MgCl_2$ pH 9.5) for 5 min or less at 37° C.

In this example, recombinant VibB has been selected using an affinity method. Tagging was conducted by the addition of a biotinylated CoA-derivative and a PPTase such as the *Bacillus subtilis* Sfp transferase. Each reaction contained 200 µL of an *E. coli* lysate containing approximately 0.12 µg of VibB. This blot was developed by transferring protein from a SDS-page gel onto PDVF and/or a nitrocellulose paper and developing by the sequential addition of a Streptavidin Alkaline Phosphatase conjugate followed by exposure to BCIP/NBT. The net protein content of the solution was stained by Coomassie blue. A gradient of biotinylated-CoA derivative was placed across the gel. Metal induction is required for the overexpression of the native EntB and EntF proteins to minimize inference when examining the overexpression of recombinant carrier proteins conventional *E. coli* expression vectors.

Example 11

Affinity Chromatography

Biotinylated CoA derivatives were incubated with crude cell lysate from VibB-producing *E. coli* (as described above) and the mixture was run over a small column loaded with streptavidin-linked-agarose resin. Following washing, some of the resin was boiled to release biotin-bound protein, and the sample was subjected to SDS-PAGE as well as blotting with a streptavidin-phosphatase conjugate. Both the Coomassie-stained gel and the blot demonstrated that VibB was successfully purified with biotin affinity chromatography. In addition to high affinity methods, native proteins were isolated using non-denaturing purification, for instance, the affinity between carbohydrate-tagged proteins (i.e. β-mannosylated proteins) and lectin linked-agarose resins (i.e., concanavalin A). Bound protein was eluted off the agarose with a gradient of carbohydrate (i.e., mannose for beta-mannosylated proteins), and the purified protein was identified with SDS-PAGE and blot against a lectin peroxidase conjugate (i.e., concanavalin A-peroxidase conjugate). This protocol produced pure, non-denatured VibB tagged with mannose. This protocol can be conducted with any affinity tag and molecular binding partner, including mannose-concanavalin A, peptide-antibody, and or peptide-protein interactions. These results were reproduced using mannose-linked CoA tagging to VibB with Sfp, isolating on Concanavalin A-linked agarose column, and eluting with increasing concentrations of free mannose. This technique has the benefit of providing non-denatured protein, which can be further manipulated by enzyme activity assays to reporter individual domains, modules, or full synthase activity.

A 200 µL aliquot of cell culture induced with IPTG to overexpress recombinant EntB or VibB was combined with 40 µL of biotinylated-analog of CoA and 1 µL of 1 mg/mL purified Sfp and allowed to react for 30 min at room temp in the dark. 20 µL agarose-immobilized Streptavidin (4 mg/mL Streptavidin on 4% beaded agarose) was added to each sample and incubated at 4° C. for 1 hour with constant vigorous shaking. After centrifugation at 14,000×g for 1 min, the supernatant was decanted and the samples were washed 3 times with a solution containing 100 mM Tris-Cl pH 8.4 and 1% SDS in water. After washing, the samples were boiled in 50 mL SDS sample buffer for 10 min, centrifuged, and the supernatant run on a 12% Tris-Glycine gel.

Example 12

Removal of Tag

Once proteins containing carrier proteins have been isolated, removal of the tagged 4'-phosphopantetheine-labeled moiety can be performed in order for the carrier proteins to resume natural activity. This can be accomplished with a phosphodiesterase that cleaves the phosphate linkage between the serine of the carrier protein and the tagged pantetheine. In particular, acyl-carrier-protein phosphodiesterase (ACP-PDE), used in natural systems to remove 4'-phosphopantetheine from fatty acid acyl carrier proteins, can be used for this purpose.

Example 13

Kinetic Analysis

Proteins identified, cloned and/or isolated through this study can also be used to determine kinetic properties of a given synthetic system. Herein, the loading and transfer properties of identified and purified FA, PK, and NRP synthases can be determined in vitro. Such studies can be used to quantify the efficiency of a given PPTase/carrier protein pair as well as to determine the efficiency of PPTase activity with individual domains, individual modules, multiple modules, or complete biosynthetic systems. PPTase activity can be simply assayed through the fluorescent labeling technique described herein. Time course experiments can be conducted to determine kinetic measurements of $K_{cat}$ and $K_m$ values for individual carrier protein substrates or for individual fluorescent CoA derivatives. These techniques can also be used to determine kinetic constants for inhibitors of the 4'-phosphopantetheinylation process. These studies would involve time course experiments followed by protein precipitation via trichloroacetic acid or ammonium sulfate, wash, and fluorescent intensity measurement of tagged proteins. In addition, equilibrium based techniques such as equilibrium dialysis can also be used to identify the amount of reporter uptake as given by concentration of crypto-synthase. These data can yield rate information for further studies.

Example 14

Mechanistic Studies

Three major activities can be simply analyzed through biochemical techniques: these include (but are not limited to) posttranslational modification, amino acid or acyl monomer loading, condensation or ketosynthase, and thioesterase activity. For instance, a module isolated from a transgenic expression system and purified using mannosylated tagging, concanavalin A-agarose affinity, and untagged using a PDEase can be subsequently analyzed for in vitro 4'-phosphopantetheinylation kinetic rates with a PPTase and a fluorescent CoA derivative with a time course study. Subsequently the crypto-synthase (prepared by incubated with CoA and a PPTase) can be reported for loading in vitro: adenylation (in NRP synthase systems) or acyltransferase (in PK and FA synthase systems) activity. Here, the isolated crypto-enzymes are incubated with radiolabeled amino acids and ATP (in NRP synthase systems) or radiolabeled malonyl CoA or methylmalonyl CoA (in PK and FA synthases). These experiments can be analyzed by SDS-PAGE and phosphorimaging to determine whether the carrier protein domain is properly loaded with the proper monomer. This experiment can also be carried out with other techniques, for instance using radiolabeled pyrophosphate with NRP synthases and isolating ATP to probe for pyrophosphate exchange. Should enzymes be properly loaded, condensation activity (for NRP systems) or ketosynthase (for PK and FA systems) can be studied next. Using radiolabeled monomers pre-loaded onto the carrier proteins, a condensation/ketosynthase reactions can be identified between modules by TCA precipitation and SDS-PAGE and phosphorimaging. Alternatively, N-acetylcystanine thioesters of monomers or oligomers can be used to probe internal condensation or ketosynthase activities in a synthase. Thioesterase activities are frequently reported with the use of N-acetylcystamine thioesters of linear precursors and analyzed for cyclization or hydrolysis activity with chromatographic and mass spectroscopy methods.

Example 15

Serially Addressable Fusion Protein-Tag (SAFP-TAG) Fusion Proteins

The methods of the present invention can be used to construct the Serially Addressable Fusion Protein-Tag (SAFP-TAG) fusion protein system. A fusion protein system was created for these studies. One of the smallest polyketide carrier proteins, frnN, the frenolicin acyl CP from S. roseofulvus, contains 83 amino acids and demonstrates robust expression in E. coli from a C-terminal histidine-tagged expression vector called XA. A construct XA-frnN was modified at the 3'-end of the gene to convert it to a C-terminal fusion vector pDESTc-frnN. To create the N-terminal fusion, the gene was subcloned to include the natural stop codon back into XA and modify the construct at the 5'-end of the gene to create pDESTn-frnN. These two destination vectors were then used to create a variety of fusion proteins from both eukaryotic and prokaryotic genes.

Modifying enzymes have been screened for optimal labeling kinetics. Over 200 PPTase sequences have been annotated in the Genbank, and thousands more are accessible from NRP and PK expressing organisms. 15-20 of these PPTases were cloned and sequenced from several bacterial and filamentous fungal species. Literature precedent has demonstrated that some PPTases display selective recognition of CP domains.

For example, while it is well established that the *E. coli* PPTase EntD, responsible for modifying EntB, it is not sufficient for other secondary metabolic CP domains. This mechanism allows the selectivity to be engineered with terms regulating the choice of CP domain and reporter undergoing the labeling reaction.

Organisms with PPTase sequences in Genbank were obtained from the American Type Culture Collection (ATCC), grown with appropriate conditions, and genomic DNA was isolated through a general benzyl chloride procedure followed by amplification, cloning, and expression. These studies will be followed by PPTase activity studies involving fluorescent and chemical reporters of various sizes and chemical attributes.

Affinity reporters can be screened for manipulation of tagged fusion proteins. Several fluorescent and affinity reporter molecules have been used. However, almost any biocompatible molecule can be attached to the CP domain in the compositions and methods of the present invention. A variety of CoA reporter analogs will be synthesized for visualization and affinity uses. These will include, but are not limited to, peptide tags, such as poly-histidine; carbohydrate tags, such as cellulose and sialyl-Lewis$^x$; metal-tags, such as chelated mercury and nickel; DNA tags containing both single- and double-stranded fusions; lipid tags, including myristate, palmitate, and other bioactive fatty acids; radioactive tags with $^3$H, $^{35}$S, $^{32}$P, or $^{14}$C labeled molecules.

Example 16

Synthesis and Evaluation of Bioorthogonal Pantetheine Analogs for in Vivo Protein Modification In vivo carrier protein tagging has recently become an attractive target for the site-specific modification of fusion systems and new approaches to natural product proteomics. A detailed study of pantetheine analogs was performed in order to identify suitable partners for covalent protein labeling inside living cells. A rapid synthesis of pantethenamide analogs was developed and used to produce a panel which was evaluated for in vitro and in vivo protein labeling. Kinetic comparisons allowed the construction of a structure-activity relationship to pinpoint the linker, dye, and bioorthogonal reporter of choice for carrier protein labeling. Finally bioorthogonal pantetheine analogs were shown to target carrier protein with high specificity in vivo, and undergo chemoselective ligation to reporters in crude cell lysate. The methods demonstrated here allow carrier proteins to be visualized and isolated for the first time without the need for antibody techniques and set the stage for the routine use of carrier protein fusions in chemical biology.

Recent years have seen intense research effort focused towards development of new methods for the study and manipulation of covalently modified proteins, with particular attention given to in vivo methodologies. Bertozzi et al., *Nat. Chem Biol.* 1:13, 2005. Fluorescent protein fusions and antibody conjugates provide powerful tools for protein imaging and manipulation. Tsien, *Annu. Rev. Biochem.* 67:509, 1998; Lippincott-Schwartz et al., Science 300:87, 2003; Fritze et al., *Meth. Enzymol.* 327:3, 2000 and Massoud et al., *Genes Dev.* 17:545, 2003. However drawbacks of these methods, such as structural perturbations sometimes induced by large fusions and general membrane impermeability of antibodies, have lead researchers to devise methods for the site-specific modification of proteins by small-molecule probes. Ideally these probes should be low molecular weight, covalent in nature, and possessed of fluorescence or affinity properties allowing for facile imaging and manipulation. One such technique was recently introduced to demonstrate cellular uptake and covalent modification of carrier protein fusions by pantetheine analogs. Clarke et al. *J. Am. Chem. Soc.* 127:11234, 2005. These coenzyme A (CoA) precursors were shown to penetrate the cell membrane and be transformed into fully formed CoA derivatives via the endogenous CoA metabolic pathway, whereupon they were transferred to a carrier protein by the promiscuous phosphopantetheinyltransferase (PPTase) Sfp. This advance allows carrier protein labeling, a technique first developed from cell lysates and since demonstrated on the cell surface, to be performed within the cell, opening the door for more sophisticated labeling systems. La Clair et al., *Chem. Biol.* 11: 195, 2004; Yin et al., *J. Am. Chem. Soc.* 126:7754, 2004; Yin et al., *J. Am. Chem. Soc.* 126:3570, 2004; George et al., *J. Am. Chem. Soc.* 126:8896, 2004; Yin et al., *Chem. Biol.* 12:199, 2005 and Vivero-Pol et al., *J. Am. Chem. Soc.* 127:12770, 2005. Recent developments have seen the trimming of the carrier protein domain down to just eleven amino acids, offering a fusion tag of the size and flexibility to be competitive with contemporary tagging systems and further highlighting the importance of techniques for the labeling of intracellular carrier proteins. Yin et al., *Proc. Natl. Acad. Sci. U.S.A.* 102:15815, 2005.

Example 17

Strategies for Site-Specific Labeling of Proteins In Vivo

Several strategies for site-specific labeling of proteins in vivo have been previously demonstrated. Examples include Bertozzi's manipulation of the sialic acid biosynthetic pathway for the introduction of keto and azido functionalized cell-surface glycoproteins, Cravatt's introduction of azido/alkyne functionalities by covalent irreversible inhibition of protein active sites, and Hsieh-Wilson's chemoenzymatic introduction of a keto-functionality for capture of O-GlcNAc-modified proteins. Mahal et al., *Science* 276:1125, 1997; Yarema et al., *J. Biol. Chem.* 273:31168, 1998; Saxon and Bertozi, *Science* 287:2007, 2000; Speers and Cravatt, *Chem. Biol.* 11:535, 2004; Speers et al., *J. Am. Chem. Soc.* 125:4686, 2003; Alexander and Cravatt, *Chem Biol.* 12:1179, 2005; Hwan-Ching et al., *J. Am. Chem. Soc.* 126:10500, 2004; Khidekel et al., *Proc. Natl. Acad. Sci. U.S.A.* 36:13132, 2004. In each of these examples the protein is not directly labeled with a fluorescence or affinity tag, but rather a unique and biologically inert chemical functionality is introduced. This functionality can then undergo reaction with exogenously delivered reporters to label the protein of interest for detection and/or isolation, depending on the nature of the reporter. Advantages of this two-step labeling process include (i) better uptake of smaller probes due to increased membrane permeability, (ii) increased incorporation of probes into native biosynthetic pathways due to greater similarity to natural substrate, and (iii) the ability to conjugate a protein to virtually any reporter possessing reactivity with the bioorthogonal functionality. Bertozzi et al., *Nat. Chem Biol.* 1:13, 2005; Speers and Cravatt, *Chem. Biol.* 11:535, 2004; Speers et al., *J. Am. Chem. Soc.* 125:4686, 2003; Alexander and Cravatt, *Chem Biol.* 12:1179, 2005. Here a full study of simplified pantetheine analogs that harness the power of such bioorthogonal ligation reactions is presented. First the synthesis of simplified pantetheine analogs via a one-step reaction with pantolactone was optimized. Next, the specificity of the CoA biosynthetic pathway is probed by a small panel of these simplified substrates. Finally, the utility of this strategy was validated by demonstrating and comparing the delivery of bioorthogonal chemical functionalities to carrier proteins in vitro and in vivo and using the newly tagged carrier proteins for two widely applied chemoselective ligations: the reaction of ketones and hydroxylamines to form oximes, and the Cu(I)-catalyzed azide-alkyne [3+2] cycloaddition reaction ("click" chemistry). This new ability to manipulate bioorthogonally tagged carrier protein in vivo promises to be a valuable tool for both new approaches to natural product proteomics as well as the study of novel intracellular carrier protein fusion systems.

Example 18

Analog Synthesis—Pantolactone-Ring Opening

In efforts to address CoA biosynthesis with novel analogs, the synthesis of pantetheine and phosphopantetheine analogs that could be assembled in a manner analogous to peptide library synthesis was initially investigated. Mandel et al., *Org. Lett.* 6:4801, 2004. This necessitated addressing the synthetic challenges associated with pantolactone, namely the liability of the α-proton following protection of the pantolactone secondary alcohol. At this point, the presumption was made that the identity of cystamine and β-alanine were necessary for turnover by the CoA metabolic pathway. However in vitro studies and recent work by Lee, indicated that little selectivity is gained through specific interactions between the β-alanine moiety of pantothenate and PanK, the first enzyme in the CoA biosynthetic pathway and the gatekeeper for downstream metabolism. Virga et al., *Bioorg. Med. Chem.* 14:1007, 2006; Jackowski and Rock, *J. Bacteriol.* 148:926, 1981. Further, *E. coli* PanK (COAA) was found to catalyze the phosphorylation of pantetheine and analogs with variations at the cystamine moiety almost as well as pantothenate itself. Worthington and Burkart, *Org. Biomol. Chem.* 4:44, 2005. Given this newly revealed permissiveness in the CoA biosynthetic pathway, it was reasoned that simplified analogs of pantetheine could be used for both in vitro and in vivo applications. Elimination of the amide bond between cystamine and β-alanine significantly simplifies synthetic access to reporter-modified pantetheine analogs by reducing overall molecule polarity and solubility issues, eliminating time-consuming protection/deprotection steps of the 1,3-diol, and replacing the multiple peptide coupling and purification steps of previous syntheses with a simple one-step nucleophilic ring-opening of pantolactone. Clarke et al., *J. Am. Chem. Soc.* 127:11234, 2005. With this in mind the aletheine moiety (N-(β-Alanyl)-β-aminoethanethiol) was mimicked with more synthetically flexible polyethylene glycol (PEG) linkers. In addition to the synthetic utility of this substitution, PEG spacers have the advantages of increasing aqueous solubility of small molecule probes and distancing reporter labels from labeled protein with the effect of both enhancing secondary detection properties and reducing any negative effect of reporter/protein interactions. Kumar and Aldrich, *Org. Lett.* 5:613, 2003. These advantages were incorporated into the design of an ideal, synthetically straightforward, biodetectible pantetheine analog.

In order to quickly access a large selection of analogs it was deemed appropriate to first revise the current methodology for pantothenamide synthesis. Previous protocols calling for the base-promoted nucleophilic ring opening of pantolactone by an amine could be subject to racemization or hampered by long reaction times (>24 hrs). Virga et al., *Bioorg. Med. Chem.* 14:1007, 2006; Dueno et al., *Tet. Lett.* 40:1843, 1999; Michelson, *Biochim. Biophys. Acta*, 93:71, 1964; Moffatt and Khorana, *J. Am. Chem. Soc.*, 83:663, 1961. To address these problems, microwave-assisted organic synthesis was employed. By using (S)-(−)-α-methylbenzylamine one can test a variety of conditions for their ability to open pantolactone with a fairly hindered chiral nucleophile and analyze enantiopurity by $^1$H-NMR (Table 1, see supporting information for $^1$H-NMR data). Bertozzi et al., *Nat. Chem. Biol.* 1:13, 2005.

TABLE 1

Data table for 1-step synthesis of pantetheine analogs via nucleophilic ring opening of pantolactone.

| Amine | Solvent | Temp (° C.) | Time (hr) | Yield |
|---|---|---|---|---|
| (19) | EtOH | 160(a) | 0.5 | 91% |

TABLE 1-continued

Data table for 1-step synthesis of pantetheine analogs via nucleophilic ring opening of pantolactone.

| Amine | Solvent | Temp (° C.) | Time (hr) | Yield |
|---|---|---|---|---|
| (19) | DMF | 165(a) | 0.5 | 63% |
| (19) | THF | 110(a) | 0.5 | 44% |
| (41) | EtOH | 160 (a) | 0.5 | 42% |
| (44) | EtOH | 160 (a) | 0.5 | 82% |
| (20) | EtOH | 160 (a) | 0.5 | 75% |
| (19) | EtOH | Reflux (b) | 7 | 97% |
| (19) | MeOH | Reflux (b) | 7 | 84% |

TABLE 1-continued

Data table for 1-step synthesis of pantetheine analogs via nucleophilic ring opening of pantolactone.

| Amine | Solvent | Temp (° C.) | Time (hr) | Yield |
|---|---|---|---|---|
| (19) | CH$_3$CN | Reflux (b) | 22 | 83% |
| (19) | DME | Reflux (b) | 12 | 30% |

(a) Microwave-assisted.
(b) Thermal condition.

The study showed pantolactone to be surprisingly robust to a variety of conditions, and reaction times could be reduced nearly 50-fold compared to previous preparations with retention of optical purity. As expected from the hypothesized transition state of this reaction, protic solvents proved ideal for nucleophilic ring-opening, with ethanol providing the best balance of energy-absorbance and solubilization. Moving from this model-system to usefully functionalized amines, it was shown that alkyne (41), PEG (44), and fluorophore (20) containing pantetheine analogs could be synthesized in good to moderate yield within 30 minutes using microwave-assistance. Interestingly a very recent report also presented ethanol as the solvent of choice for this transformation under thermal conditions; however without the addition of any base these large-scale syntheses suffered from very long reaction times (72-120 hrs). Krause et al., *Syn. Comm.* 36:365, 2006. Accordingly the ideal microwave reaction conditions were also tested under simple reflux. Triethylamine proved to be a sufficient base, as replacement with Hunig's base showed no significant effect on reaction outcome. Stronger bases were avoided. Again it was found that reflux of (S)-(−)-α-methyl-benzylamine with excess pantolactone and triethylamine provided pantetheine analogs with no apparent racemization in excellent yields in 7-12 hours. This alternative synthesis provides another avenue for analog preparation in cases where the reporter or linker is sensitive to decomposition under microwave conditions. Microwave-assisted conjugation of 7-dimethylaminocoumarin-4-acetic acid containing amines to pantolactone resulted in the formation of unidentified decomposition products. For these couplings the classical condition (MeOH, NEt$_3$, reflux) was used.

Example 19

Synthesis of Bioorthogonal and Fluorescent Pantetheine Analogs

Figure 7:
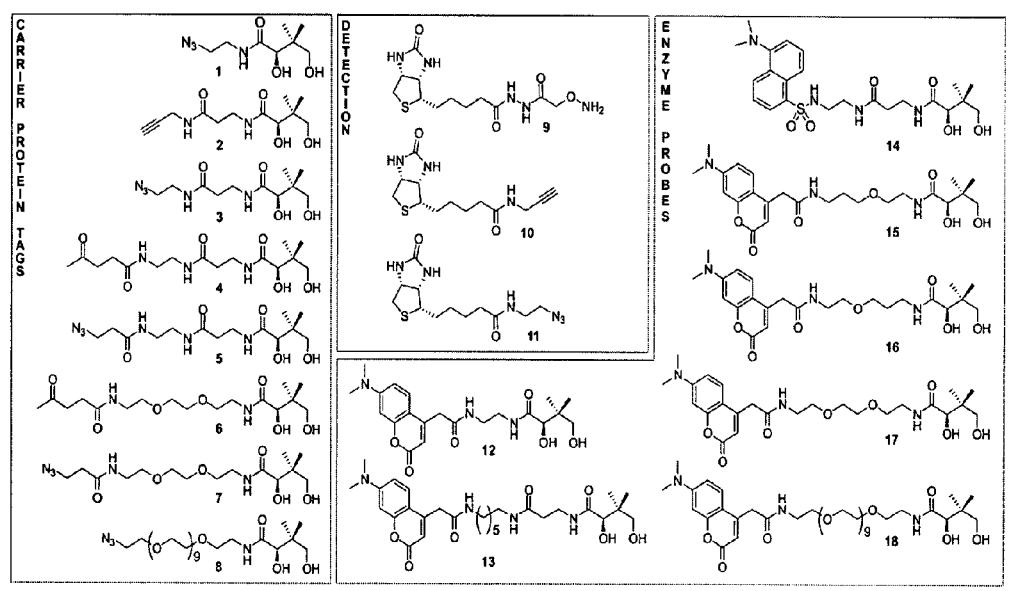
FIG. 7 shows structures of pantetheine analogs and biotin detection agents used in this study.
Figure 8:
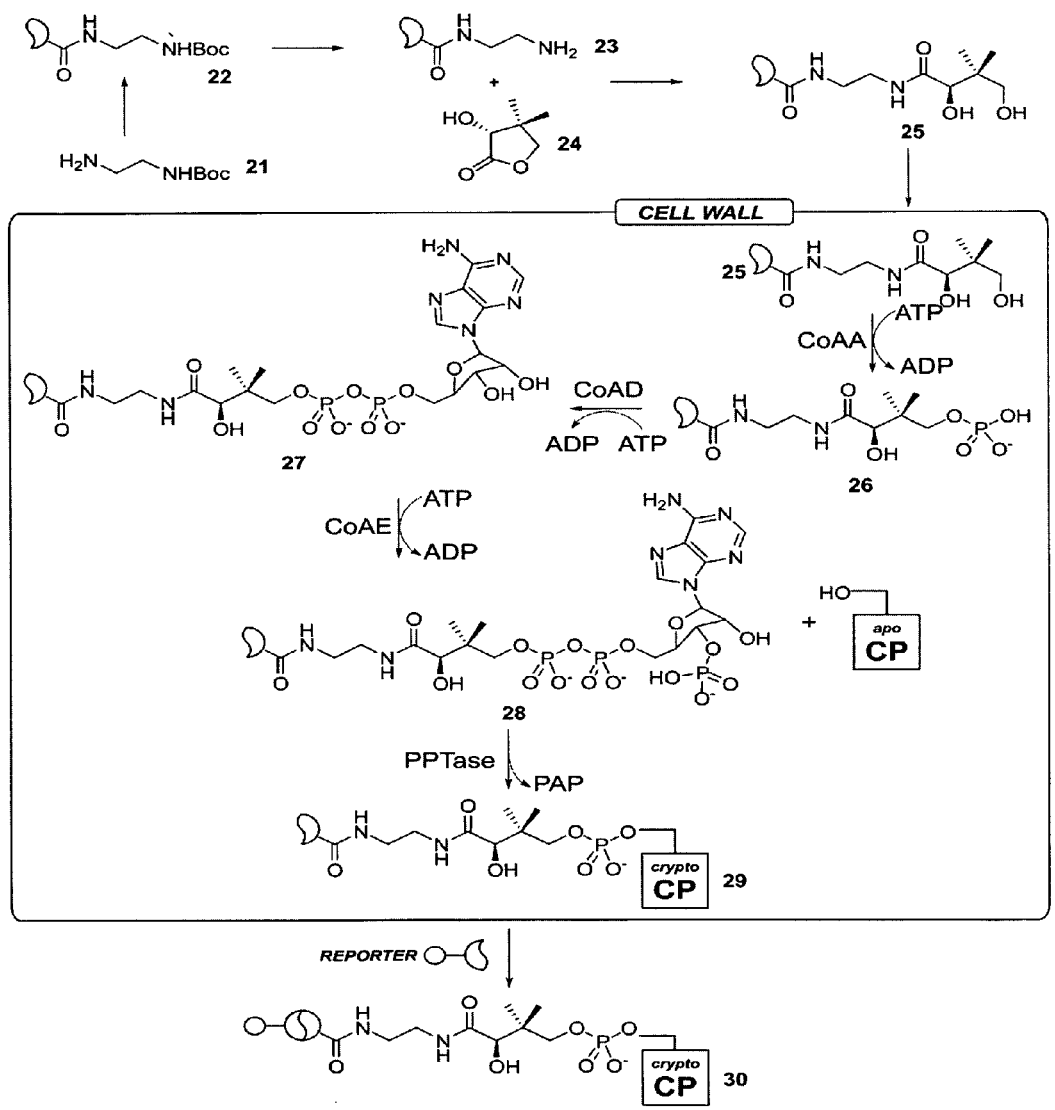
FIG. 8 shows a general strategy for in vivo labeling of carrier protein by pantetheine analogs.

The general strategy for chemoenzymatic synthesis of CoA analogs is depicted in FIGS. 7 and 8. FIG. 7 shows structures of pantetheine analogs and biotin detection agents used in this study. FIG. 8 shows a general strategy for in vivo labeling of carrier protein by pantetheine analogs. Virtually any mono-protected amine (21) can be transformed into a pantetheine analog (25) by the three-step coupling/deprotection/ring-opening sequence. Cellular uptake and biosynthetic processing by CoAA, CoAD, and CoAE yields the CoA analog 28, which is then transferred to the carrier protein by a PPTase to yield bioorthogonally labeled carrier protein 29. After cell lysis this carrier protein can now be conjugated to the reporter of choice via an appropriate chemoselective ligation reaction.

First a mono-protected amine (depicted in this example by N-Boc ethylenediamine 21) is conjugated to the biodetectible tag of choice by standard peptide coupling conditions. After deprotection, this amine can be conjugated to either pantolactone 24 through nucleophilic ring opening or pantothenic acid via EDAC mediated coupling. The newly formed pantetheine analog is then processed via stepwise conversion by CoAA, CoAD, and CoAE to form CoA analog 28, which is subsequently transferred to a conserved residue of the carrier protein by a PPTase to produce reporter-modified crypto-carrier protein 30.

Analogs 12-18 were synthesized by this route in order to test the permissibility of CoA biosynthesis toward unnatural pantetheine analogs, particularly the effect of changes in the β-alanine/cystamine region (Scheme 3). Three parallel amino-protecting group strategies (azide, Boc, Alloc) were chosen based on the commercial availability (32a), simple synthesis from literature preparations (33c, 34e), and orthogonal protecting group traits (32b, 33d) of the specified diamines. This strategy allowed compound 12 to be synthesized in two steps from N-Boc ethylenediamine conjugated 7-dimethylaminocoumarin-4-acetic acid (DMACA) 36c. La Clair et al. *Chem Bio Chem* 7:409, 2006. Acid-catalyzed deprotection afforded the free amine, which performed nucleophilic ring opening of pantolactone to afford the final product in 85% yield. Compound 13 was synthesized as previously described, while dansylated pantetheine 14 was synthesized by an analogous route. Clarke et al., *J. Am. Chem. Soc.* 127:11234, 2005. Compounds 15 and 16 were chosen to probe the effect of replacement of the strong H-bond accepting carbonyl and H-bond donating nitrogen of the natural substrate amide with weak H-bond accepting ether oxygens. Their synthesis made use of a common orthogonally protected diamine 48 (see supporting information); which underwent differential deprotection to give mono-protected diamines 32b and 33d. Subsequent EDAC mediated conjugation to dye 31, azido/Boc deprotection by standard conditions, and nucleophilic ring opening of pantolactone afforded enzyme probes 15 and 16. Preliminary studies of PEG-linked-pantoic acid conjugates showed good activity in in vitro assays, leading us to synthesize 17 in a 41% overall yield through an analogous dye conjugation/deprotection/nucleophilic ring-opening sequence starting with the previously described N-Alloc diaminoethylene glycol 34e. Compound 18 was chosen to test the limits of linker-length in CoA biosynthesis and was easily attainable from the commercially available mono-azido/mono-amino terminal nonaethylene glycol 32a through a similar series of reactions.

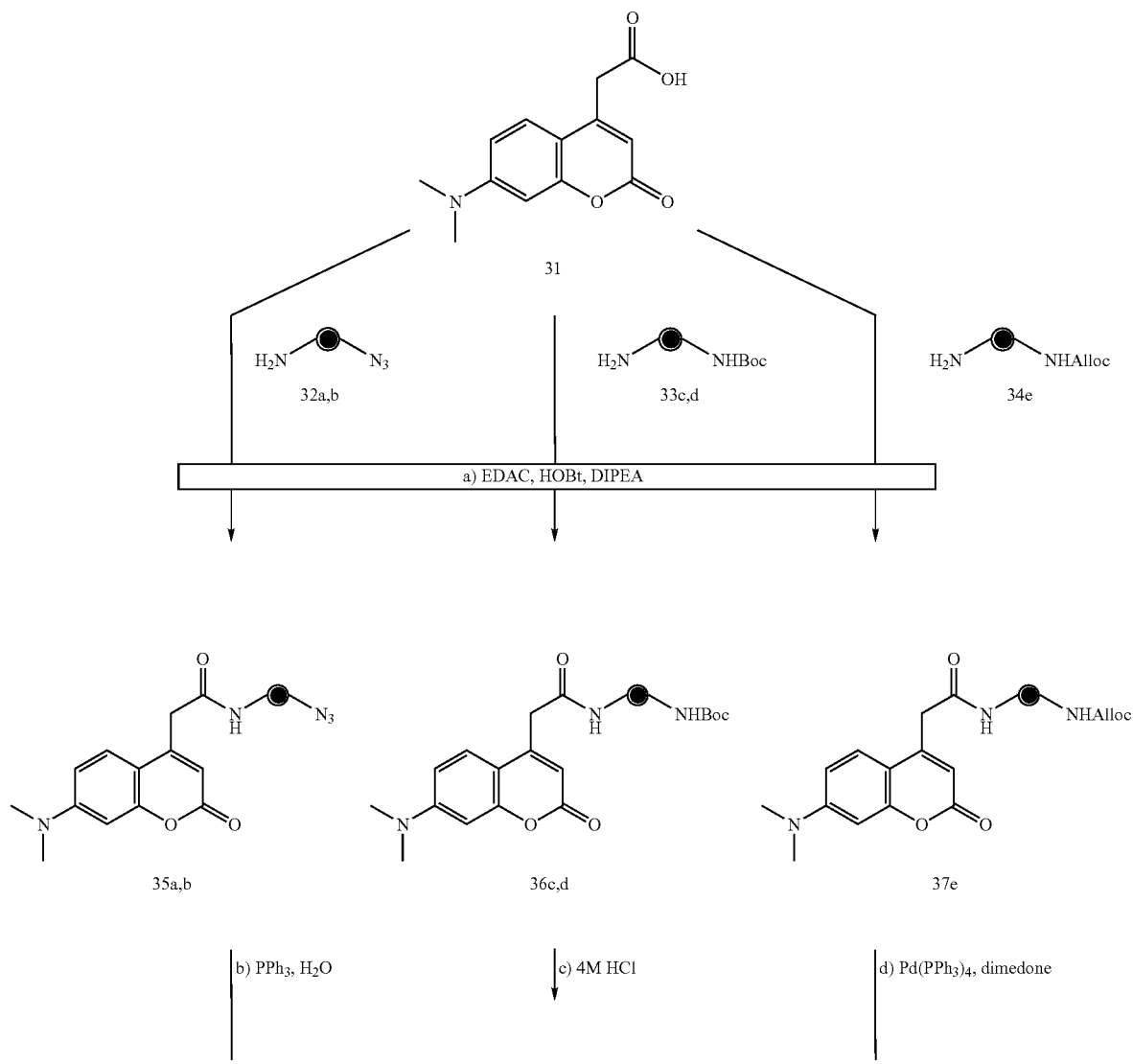

Scheme 1. Synthesis of PanK Probes.

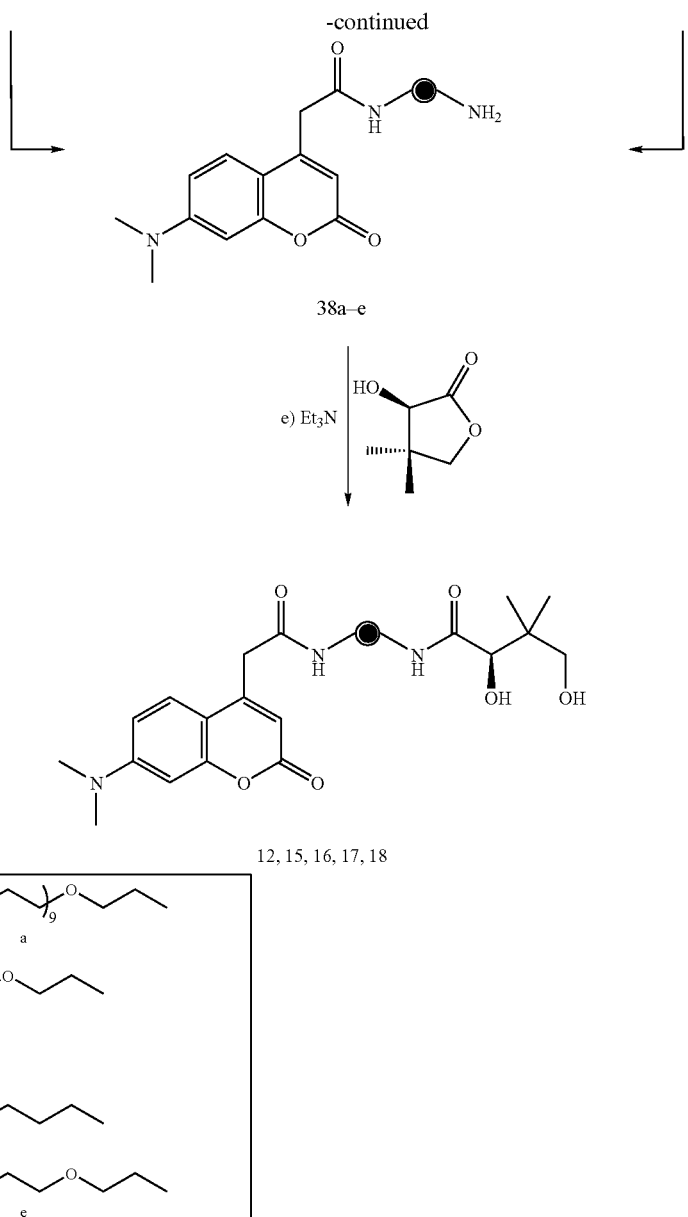

(a) EDAC (2 eq), DIPEA (2 eq), DMF, rt 12 h (b) PPh₃ (1.2 eq), 10:1 THF/H₂O rt 12-24 h (c) 4M HCl/dioxanes, rt 24 h (d) Pd(PPh₃)₄ (cat.), PPh₃ (2 eq) dimedone (7 eq) rt 12 h (e) pantolactone (3 eq), NEt₃ (3 eq), MeOH, reflux 24-72 h Compounds 1-8 sought to create a wide-spectrum of pantetheine analogs incorporating some of the most commonly used bioorthogonal tags such as ketones, azides, and alkynes. Particular attention was paid to the azido-moiety, where analogs replacing the β-Ala (1), cystamine (2), and thio-acetal (5) regions of natural pantetheine with terminal azide moieties were synthesized, in addition to experimentation with short (7) and long (8) PEG-linked azido-pantetheine analogs. Compound 1 was synthesized in one step from the nucleophilic ring-opening of pantolactone by 2-azidoethanamine (42). Compounds 2 and 3 (Scheme 2) were synthesized by standard peptide coupling of p-methoxybenzylacetal-protected (PMP) pantothenate 39 and the corresponding alkynyl and azido-amines, followed by acidic deprotection of the 1,3-diol. Compounds 4 and 5 again utilized 39 as a starting material, which was coupled to 2-azidoethanamine, deprotected to the corresponding amine, and coupled to the corresponding N-hydroxysuccinimidyl keto/azido (43a,b) ester. PEG linked pantetheine conjugates 6 and 7 (Scheme 3) were constructed in a similar fashion by nucleophilic ring-opening of pantolactone under microwave-conditions by N-Alloc protected diaminoethylene glycol 44 to give a common intermediate, followed by Pd(PPh₃)₄ mediated deprotection and coupling of the purified free amine to an keto/azido acid activated as the succinimidyl ester. Finally, analog 8 was synthesized in one step through microwave-assisted nucleophilic ring-opening of pantolactone by mono-azido/mono-amino terminated nonaethylene glycol 32a.

Scheme 2. Synthesis of β-Ala Linked Bioorgthogonal Pantetheine Analogs.

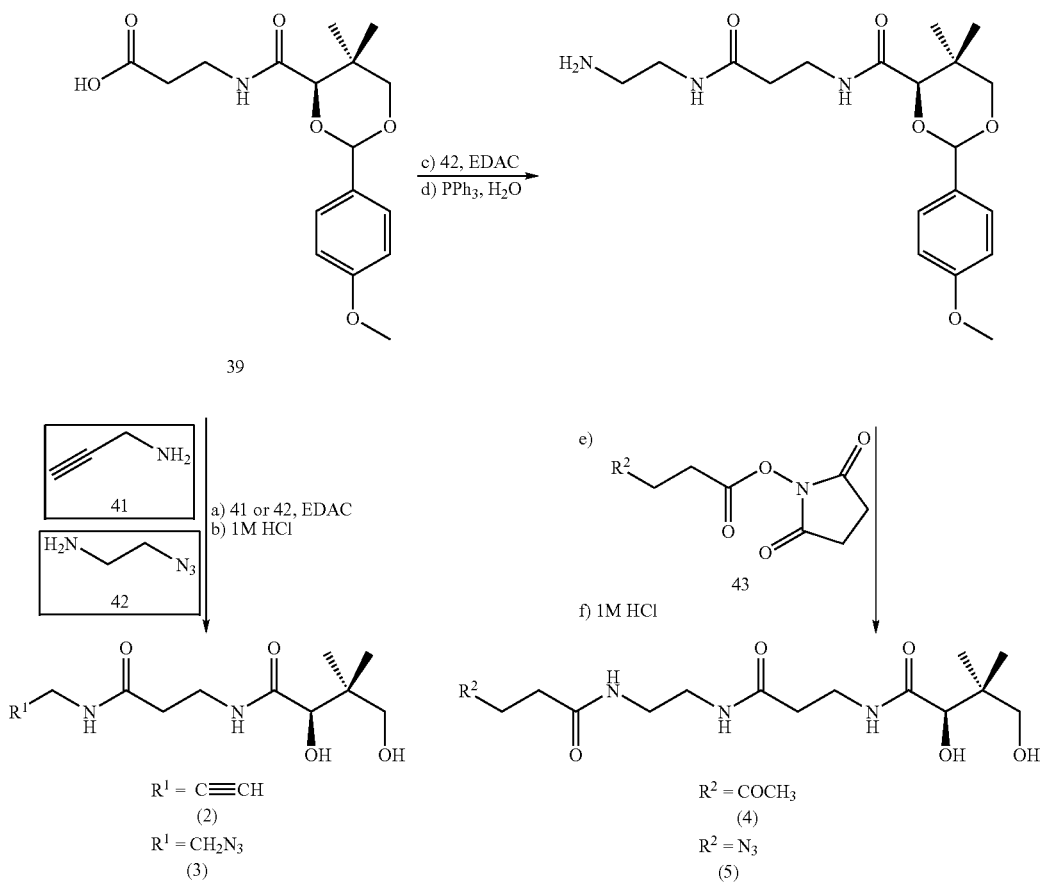

(a) 41 or 42, EDAC (2 eq), HOBt (2.5 eq), DIPEA (2 eq), DMF, rt 12 h (b) 1M HCl, 1:1 THF/H₂O rt 1 h (c) 42, EDAC (2 eq), HOBt (2.5 eq), DIPEA (2 eq), DMF, rt 12 h, (d) PPh₃ (2 eq), 10:1 THF/H₂O, rt 12 h (e) NHS ester 43a or 43b, NEt₃ (2 eq), rt 8 h, (f) 1M HCl, 1:1 THF/H2O rt 1 h.

Scheme 3. Synthesis of PEG-linked Bioorthogonal Pantetheine Analogs.

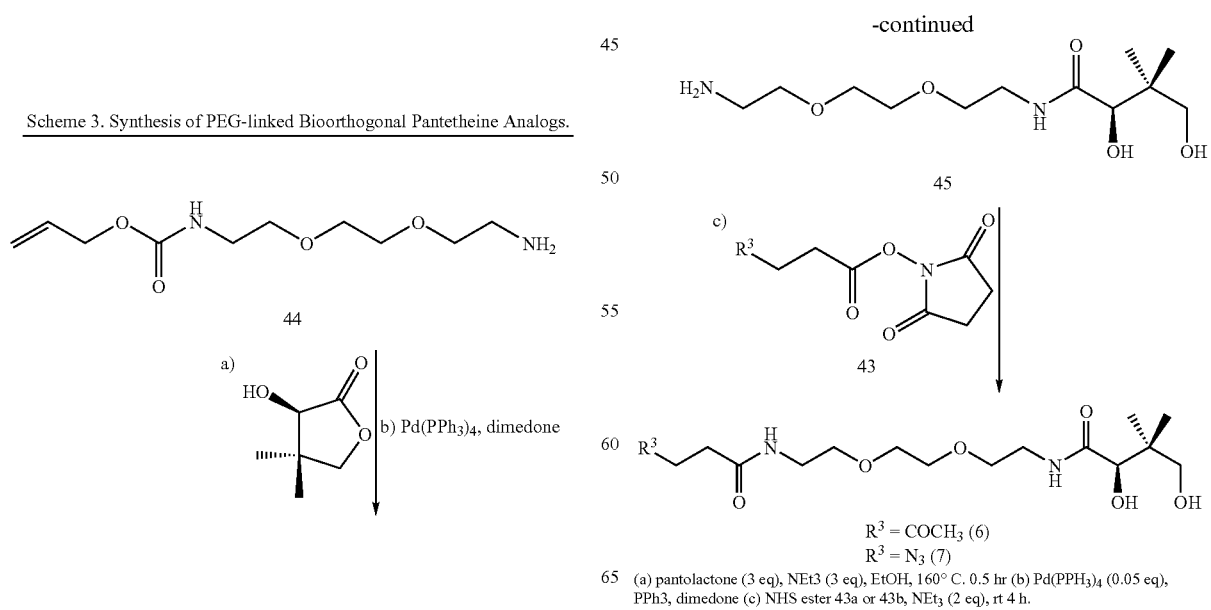

(a) pantolactone (3 eq), NEt3 (3 eq), EtOH, 160° C. 0.5 hr (b) Pd(PPH3)4 (0.05 eq), PPh3, dimedone (c) NHS ester 43a or 43b, NEt3 (2 eq), rt 4 h.

Example 20

In Vitro Pathway Uptake: Kinetics with CoAA

As mentioned earlier, phosphorylation of the primary hydroxyl group of pantothenate by the first protein in the CoA biosynthesis pathway, PanK, is believed to be the rate limiting step in vivo. Jackowski and Rock, *J. Bacteriol.* 148:926, 1981. Due to its role as the gatekeeper of CoA biosynthesis, each of the new analogs was assayed for kinetic activity with PanK (Table 2).

TABLE 2

Kinetic parameters of *E. coli* PanK with natural substrates and pantetheine analogs.

| Compound # | $k_{cat}$ (min$^{-1}$) | $K_m$ (μM) | $k_{cat}/K_m$ (s$^{-1}$ mM$^{-1}$) |
|---|---|---|---|
| Pantothenate | 31.27 ± 0.58 | 28.56 ± 1.77 | 18.25 ± 0.68 |
| Pantetheine[14] | 19.2 ± 0.1 | 91 ± 10 | 3.53 ± 0.44 |
| 1 | 22.33 ± 1.54 | 692.3 ± 89.13 | 0.54 ± 0.07 |
| 2 | 31.45 ± 0.75 | 32.85 ± 2.54 | 15.96 ± 0.76 |
| 3 | 28.017 ± 0.42 | 43.53 ± 1.99 | 10.73 ± 0.32 |
| 4 | 20.64 ± 0.45 | 62.65 ± 3.89 | 5.49 ± 0.24 |
| 5 | 40.91 ± 1.12 | 71.89 ± 6.98 | 9.48 ± 0.52 |
| 6 | 1.60 ± 0.06 | 0.1955 ± 0.09 | 136.4 ± 10.63 |
| 7 | 6.16 ± 0.44 | 53.76 ± 11.16 | 1.91 ± 0.27 |
| 8 | NA | NA | NA |
| 12 | 11.56 ± 0.57 | 37.24 ± 5.82 | 5.17 ± 0.51 |
| 13 | 19.16 ± 1.41 | 28.40 ± 6.92 | 11.25 ± 1.65 |
| 14 | 17.26 ± 0.62 | 27.33 ± 3.28 | 10.53 ± 0.76 |
| 15 | 1.36 ± 0.05 | 0.76 ± 0.32 | 0.03 ± 0.04 |
| 16 | 1.00 ± 0.03 | 0.14 ± 0.18 | 0.12 ± 0.01 |
| 17 | 10.06 ± 0.43 | 51.18 ± 6.42 | 3.28 ± 0.28 |
| 18 | NA | NA | NA |

The assay was performed as previously described using the prototypical bacterial PanK, CoAA from *E. coli*. Kumar and Aldrich, *Org. Lett.* 5:613, 2003. The reaction of CoAA with the natural substrate pantothenate gave values that conformed to those previously reported in the literature. Worthington and Burkart, *Org. Biomol. Chem.* 4:44, 2005; Strauss and Begley, *J. Biol. Chem.* 277:48205, 2002. Pantothenate mimics 2 and 3 show $k_{cat}$ and $K_m$ values closely approaching those of the natural substrate. As seen in previous studies pantetheine is also a substrate for CoAA, and compounds 4, 5, 13, and 14 show turnover near equal (4, 13, 14) or exceeding (5) that of the natural substrate in these cases. Compounds 5, 13, and 14 are processed particularly efficiently by PanK. Conversely, compounds with PEG linkers between the pantoic acid moiety and the bioorthogonal terminus were poor substrates for CoAA. The length of the linker region was a strong factor in determining substrate suitability, with the longest compounds 8 and 18 proving such poor substrates that kinetic data could not be generated. Shorter PEG linked compounds (7 and 17) were viable substrates in the assay, but turned over at a rate 2-5 fold less than derivatives containing β-Ala/diamine linkers. PEG linked pantoic acid conjugate 6 differs only from 7 by the exchange of an azide for an acyl substitutent, but shows markedly decreased kinetic activity.

To isolate and investigate the effect of H-bond accepting heteroatoms in the linker region, pantetheine analogs 15 and 16 were synthesized. These compounds were designed to replace the amide bond between β-Ala and cystamine of pantetheine with a single ether oxygen, allowing investigation of subtle substrate-enzyme interactions in the PanK active site. Virga et al., *Bioorg. Med. Chem.* 14:1007, 2006. Surprisingly, these compounds were extremely poor substrates. While compounds with the aforementioned short PEG linkers (7, 17) showed $K_m$ values two-fold higher than natural substrate pantothenate, and compounds with traditional β-Ala/diamine linkers were either the same as (13, 14) or two fold higher (4, 5), the $K_m$ values for 15 and 16 were 100-fold lower. Turnover for these compounds was proportionately low, indicative of tight binding. To test if these compounds were acting as inhibitors of CoAA, a competitive kinetic assay was set up using pantotenate as the substrate. The results (see supporting information) show that 15 acts as a non-competitive inhibitor, suggesting that it may bind the allosteric regulation site of CoAA. Ivey et al., *J. Biol. Chem.* 279:35622, 2004. Investigation of these compounds as potential inhibitor scaffolds is ongoing. Azide 1, which omitted entirely the β-Ala/carbon diamine or PEG linkages of other analogs showed turnover within the range of the natural substrate; however $K_m$ was 20-fold higher than pantothenate suggesting deletion of an interaction involved in active site binding. Another interesting pantoic acid analog 12, which shortened the pantoic acid-reporter linker length to four carbons and reversed the carbonyl and amide β-Ala/cystamine linkage of natural pantetheine, showed lower turnover and catalytic efficiency than analogs containing the natural β-Ala/pantoic acid linkage (5, 13, 14).

In Vitro Pathway Uptake: Gel Shift The conversion of apo-ACP to holo-ACP or reporter-modified crypto-ACP causes a change in the mobility of the protein on a non-denaturing polyacrylamide gel. Virga et al., *Bioorg. Med. Chem.* 14: 1007, 2006. In order to assay each compound for activity throughout the entire co-opted CoA pathway covalently modified carrier protein was run on a native PAGE gel and compared mobility to apo-ACP (FIG. 9a). Pantetheine analogs were reacted as previously reported with the enzymes CoAA-E to create CoA analogs, followed by the addition of the PPTase Sfp and apo-ACP. Clarke et al., *J. Am. Chem. Soc.* 127:11234, 2005. As seen in FIG. 9a, all of the compounds tested demonstrated some change in mobility with relation to apo-ACP. For most compounds full conversion to crypto-ACP is obtained; however analogs with long PEG linkers (8, 18) give multiple bands on the gel that suggest apo-protein remains.

Figure 10:
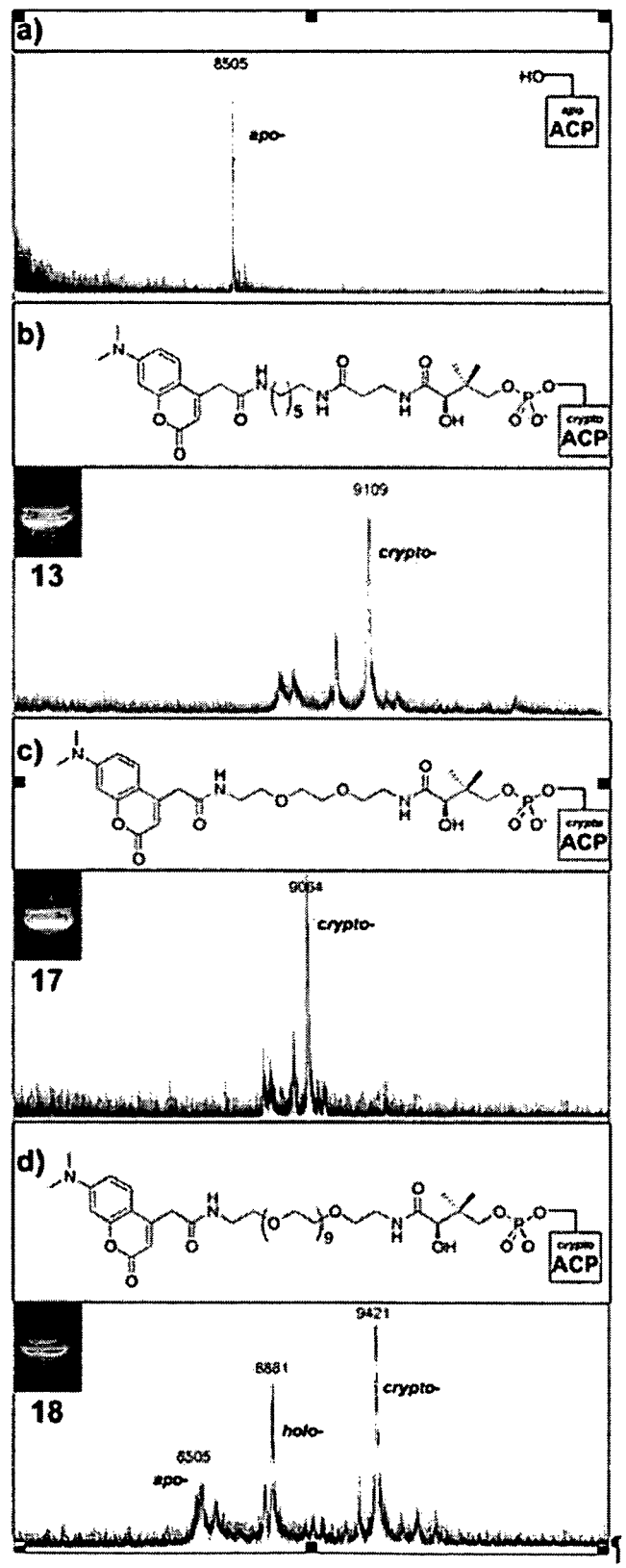
FIGS. 10a, 10b, 10c and 10d show in vitro labeling of acyl-carrier-protein (ACP).

To confirm the results from this assay, the reaction mixtures were subjected to matrix-assisted laser desorption/ionization mass spectrometry (MALDI-MS). The MALDI-MS data (FIG. 10) confirms that all pantetheine analogs in the panel are indeed converted into CoA derivatives and transferred onto carrier protein in vitro. Apo-ACP (4a) shows a characteristic peak with a mass of 8505 Da. Compound 13 was reacted with the CoAA biosynthesis enzymes, ACP, and Sfp as described above and the reaction mix analyzed by MALDI without further purification. As seen in FIG. 10b shows the reaction with the CoA analog of 13 causes the expected mass change of 604 mass units. PEG analogs 17 and 18 (FIGS. 10c,d) also show the expected mass shifts of 559 units and 916 units respectively, corresponding to the formation of crypto-carrier protein. Only in the case of the PEG-linked derivatives 8 and 18 does the conversion appear significantly incomplete, supporting the results of the gel shift assay.

In Vitro Pathway Uptake: Biodetectability Having confirmed that the pantetheine analogs were suitable substrates for the CoA biosynthesis enzymes and PPTase/carrier protein reaction, the biodetectability of each analog was investigated. The fluorescent analogs (12-18) were detected by UV visualization on PAGE gels as previously described. Clarke et al., *J. Am. Chem. Soc.* 127:11234, 2005. Bioorthogonally tagged pantetheine analogs 1-8 were detected by chemoselective ligation to the appropriate alkoxyamine/azide/alkyne functionalized biotin followed by PAGE and visualization by western blotting and incubation with streptavidin-conjugated alkaline phosphatase. Keto-pantetheine compounds 4 and 6 were reacted overnight with biotin hydroxylamine (9) at room temperature, while pantetheine analogs with azide and alkyne functionalities were reacted with the corresponding alkynyl/azido (10/11) biotin following the procedure of Alexander. Alexander and Cravatt, *Chem Biol.* 12:1179, 2005. Inspection of the fluorescent gels (FIG. 9b) and western blots (FIG. 9d) confirmed the results of the gel shift assay and mass spec data, indicating biodetectible covalent modification of carrier protein in vitro for compounds 1-8 and 12-18.

Figure 9:
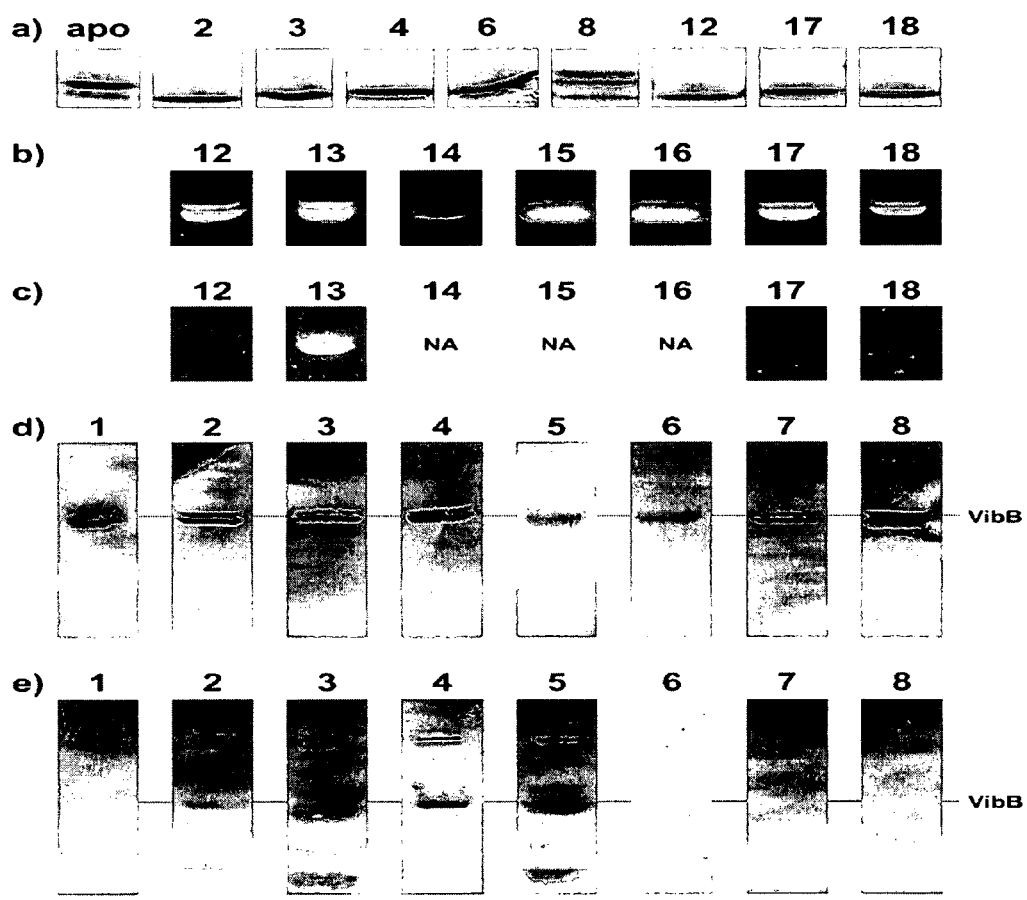
FIGS. 9a, 9b, 9c, 9d and 9e show in vivo and in vitro activity of pantetheine analog panel.

FIG. 9 shows in vivo and in vitro activity of pantetheine analog panel. (a) Analogs were assayed for gel shift after reaction with CoA biosynthesis enzymes (CoAA/D/E), PPTase (Sfp) and carrier protein (*E. coli* ACP). Conversion of apo-ACP to reporter modified crypto-ACP causes a change in the mobility of the protein on native PAGE. (b) In vitro modification of the carrier protein VibB by reaction with fluorescent pantetheine analogs, CoA biosynthesis enzymes (CoAA/D/E) and Sfp. (c) In vivo modification of carrier protein by incubation of fluorescent pantetheine analogs with *E. coli* overexpressing VibB and the PPTase Sfp. (d) In vitro modification of VibB by reaction with bioorthogonal pantetheine analogs, CoA biosynthesis enzymes (CoAA/D/E) and Sfp. Labeled carrier protein is visualized by chemoselective ligation to the appropriate biotin reporter (9-11) followed by SDS-PAGE, blotting onto nitrocellulose, and incubation with streptavidin-linked alkaline phosphatase. (e) In vivo modification of carrier protein by incubation of bioorthogonal pantetheine analogs with *E. coli* overexpressing VibB and the PPTase Sfp. Visualization as in (d).

FIG. 10 shows in vitro labeling of ACP. Apo-ACP (a) is reacted with pantetheine analogs, CoA biosynthetic enzymes (CoAA/D/E) and the PPTase Sfp. Fluorescent compounds 13 (b), 17 (c), and 18 (d) are all shown to be converted to CoA analogs and modify ACP by gel and mass spectral analysis.

Example 21

In Vivo Uptake

Figure 11:
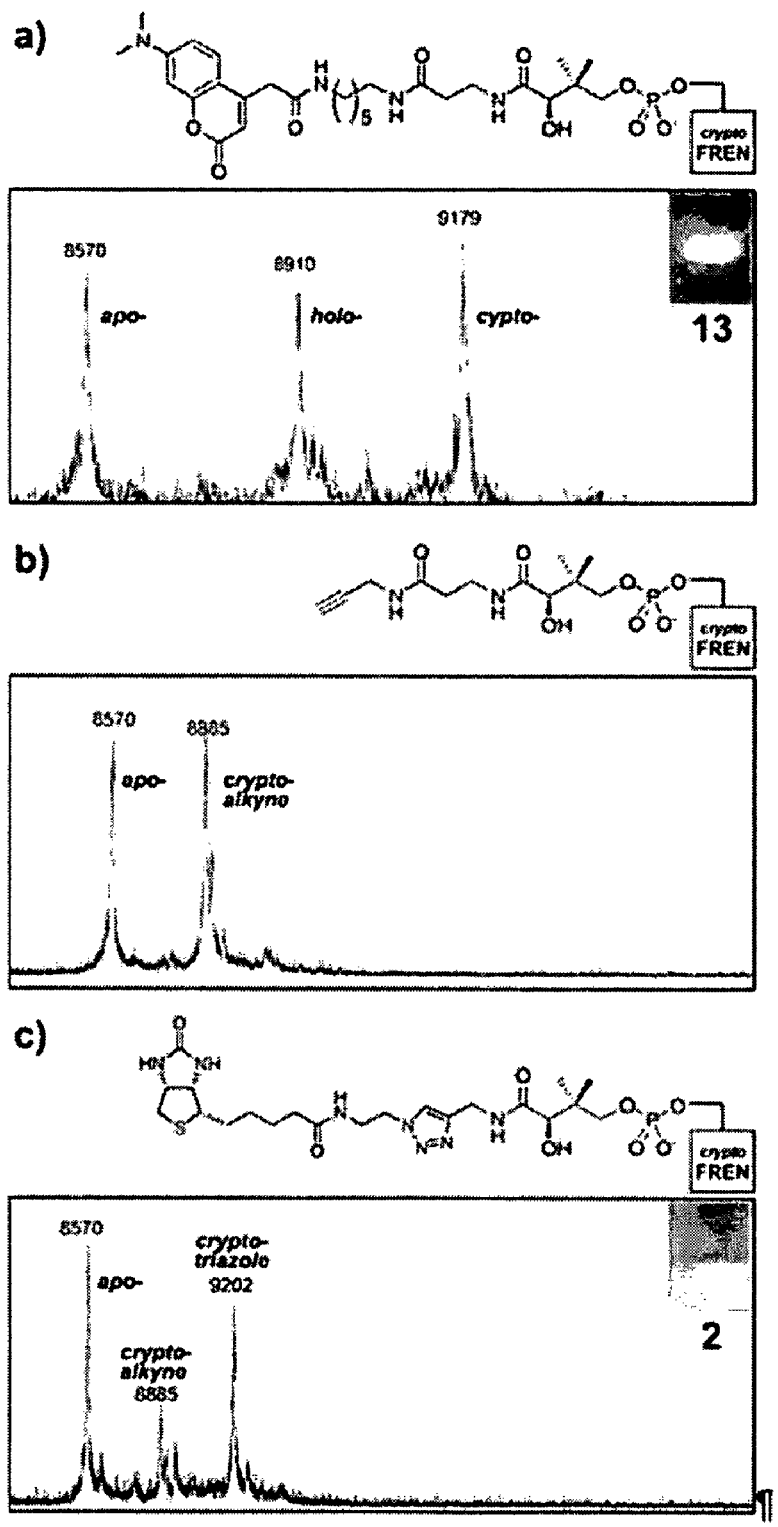
FIGS. 11a, 11b and 11c show in vivo carrier protein labeling.

The library of pantetheine analogs was tested for integration into the *E. coli* CoA pathway using an in vivo assay. Clarke et al., *J. Am. Chem. Soc.* 127:11234, 2005. *E. coli* overexpressing the carrier protein VibB and the PPTase Sfp were incubated with 1 mM of each compound in 1 ml of culture. After 4 hours of growth cells were pelleted, washed, and lysed. Lysate from these cultures was run on SDS-PAGE gels and detection carried out as described for the in vitro studies. Compounds 2, 3, 5, 12, and 13 demonstrated detectable modification of VibB in vivo (FIG. 9c/e). Keto-pantetheine analog 4 was also detectable, but showed much weaker labeling than the similarly linked azido-analog 5 (FIG. 9e). The compounds most active in vivo show a strong correlation with CoAA kinetic profile. To verify the results of the gels and blots, samples of crude lysate were assayed by MALDI-MS (FIG. 11). For MALDI-MS analysis doubly transformed *E. coli* containing plasmids for the carrier protein Fren and the PPTase Sfp were used. As seen in FIG. 11a compound 13 was taken up by the cell, processed into a CoA analog and attached onto Fren. The apo peak can be seen at 8570 mass units. A small amount of holo-carrier protein is also visible at 8910 Da. This peak arises from the fact that natural pantetheine is available in the cell and readily ligated by PPTases to the overexpressed apo-Fren. Carrier protein modified with 13 can be seen at 9179 Da giving the expected 609 mass unit change. Similarly mass spec analysis of cell lysate after incubation of bioorthogonal pantetheine analog 2 with Fren/Sfp overexpressing *E. coli* shows an observable 315 Da shift of the known apo peak indicating formation of alkyne-modified crypto-carrier protein. Subjection of the same crude cell-lysate to click reaction conditions with biotin reporter 11 resulted in another 317 Da mass shift, indicating successful formation of biotinylated Fren via a Cu(I)-catalyzed [3+2] cycloaddition process.

FIG. 11 shows in vivo carrier protein labeling. The carrier protein Fren is labeled in vivo by incubation of *E. coli* overexpressing Fren and Sfp with (a) a fluorescent pantothenate analog 13 and (b) a bioorthogonally tagged analog 2. Click reaction of alkyne-modified crypto-carrier protein with biotin reporter 11 affords triazole-linked biotinylated carrier protein (c), resulting in the expected shift in mass and allowing protein visualization by western blot.

Example 22

Insights into CoAA Substrate Specificity from Kinetic, In Vivo, and In Vitro Analyses Comparisons of the kinetic, in vitro, and in vivo assay results for different members of the panel yields important insight into the structure-activity relationships between *E. coli* PanK and pantetheine analogs. Despite the poor performance of compounds 1, 6-8, 12, and 15-18 in the PanK kinetic assay, all were shown to be converted to CoA analogs and loaded onto the carrier protein ACP by Sfp in vitro. This is both a testament to the incredible efficiency of Sfp in transferring unnatural CoA derivatives to apo-carrier proteins and a further demonstration of the utility of the chemoenzymatic approach to synthesis of unnatural CoA analogs. As mentioned above this finding greatly simplifies the synthetic task of constructing CoA derivatives for in vitro applications which utilize carrier protein tagging. George et al., *J. Am. Chem. Soc.* 126:8896, 2004; Yin et al., *Chem. Biol.* 12:199, 2005 and Vivero-Pol et al., *J. Am. Chem. Soc.* 127:12770, 2005. This allows access to virtually any reporter labeled-CoA analog from a mono-protected amine in three steps, one of which can be expedited using microwave technology. Additionally the subtle substrate preferences Sfp has been shown to exhibit in systems incorporating multiple carrier proteins can be used for selective coding based on differential phosphopantetheinylation by unnatural CoA analogs, adding another layer of complexity to in vitro and cell-surface carrier protein fusion systems. Mercer et al., *Chem Bio Chem.*, 8:1335, 2005.

Detailed analyses of the kinetic data demonstrate several important relationships. In general compounds containing a similar β-Ala linker region to natural pantothenate show the best kinetic profiles. In all compounds of the panel the pantoic acid region (C1-N5, numbering from the terminal primary hydroxyl of pantetheine) was conserved. Lee et al. indicated low binding of PanK inhibitors which lacked a proton-donating amide NH at the N8 position, pointing to a model of the PanK-ADP-pantothenate ternary complex in which the C-7 acid of pantothenate acts as an H-bond donor towards two key residues. Virga et al., *Bioorg. Med. Chem.* 14:1007, 2006; Ivey et al., *J. Biol. Chem.* 279:35622, 2004. The results verify the importance of this interaction. Compounds 1 and 3 contain the same 2-azidoethanamine-derived terminal azide, differing only in the β-Ala linkage of 3. This change results in a 10-fold increase in $K_m$ and near 20-fold increase in catalytic efficiency, indicating much better binding of the substrate with the H-bond donating β-Ala linker. Pantetheine analogs containing ethylene glycol based linkers incapable of acting as efficient H-bond donors (6-8, 17-18) showed similarly poor kinetics compared with those containing β-Ala linkers. Compounds 15 and 16 provide perhaps the strongest evidence of the importance of this interaction, losing almost all substrate activity when reducing the strength of the electron pair donor and removing the H-bond donating NH completely from the pantetheine analog. Interestingly these compounds show markedly different kinetics than PEG-linked pantetheine 17, which differs by only two atoms, demonstrating the limitations of this model in predicting effects caused by alternate variables such as the reduced rotation around an $sp^2$ hybridized carbon at C8 and addition of an extra H-bond accepting heteroatom further down the linker. The kinetics of analog 12, in which the connectivity of the amide at C8 and N9 of the natural substrate pantetheine is reversed, indicate that there is some flexibility in the pocket around this position. Compound 12 shows good binding but slow turnover, with a catalytic efficiency poorer than any of the compounds with the H-bond donator in its natural position (2-5, 13-14) but better than every compound in which the H-bond donating NH is absent (1, 6-8, 15-18). While the general trend toward an H-bond donor effect is large, other interactions resulting from the proximity of the aromatic coumarin-reporter molecule to the active site in this analog must also be considered.

Several other trends which may be important for future design of carrier protein tags are of interest. In general, analogs terminating in alkynes show better kinetic parameters than azides, and azides better than ketones. For PEG-based pantetheine derivatives, chain length proved an important factor, with longer chains showing negligible activity with CoAA and poor in vivo protein tagging. Appending a different dye to the end of the pantetheine had no statistically significant impact on CoAA kinetics; however substitution of DMACA with dansyl lead to a complete loss of in vivo activity, suggesting a possible lack of a viable membrane-transport mechanism for dansyl-pantetheine analogs or an intracellular degradation process. It has been shown previously that DMACA is an excellent dye for in vivo applications. La Clair et al., *Chem Bio Chem* 7:409, 2006. The kinetics of β-Ala containing bioorthogonal pantetheines (2-5) compared with β-Ala containing pantetheines in which a fluorescent reporter was directly appended (13-14) showed slightly better turnover and similar catalytic efficiency. On the whole the binding site of PanK beyond the β-Ala moiety appears to be quite promiscuous, with little kinetic effect observed on substitution of the hexanediamine linker of 13 with a ethylenediamine linker or substitution of the ethylenediamine linker of 14 with a short (8-atom) PEG linker. This comparison refers to kinetic data compiled for alternatively linked dansyl and DMACA-pantetheine analogs in reference 14.

Perhaps the most important conclusion that can be drawn from the assay results is that the in vivo activity of a pantetheine analog has a direct correlation with kinetic activity with PanK. Analogs 2, 3, 4, 5, 12, and 13 were shown to be biodetectible in *E. coli* by Western blot analysis and fluorescence visualization. These show a $k_{cat}$ between 11.5-40.9 $min^{-1}$ and $k_{cat}/K_m$ of 5.2-16.0 compared with the values of 31.5 $min^{-1}$ ($k_{cat}$) and 3.5 $s^{-1}$ $mM^{-1}$ ($k_{cat}/K_m$) for natural pantetheine. In order for a pantetheine analog to be processed into a CoA analog in vivo it must have comparable or better kinetics with CoAA than natural substrate pantetheine of the host. Given that enterococci produce far more pantetheine than they require for primary metabolism, any modified pantetheine analog must make extremely efficient use of CoAA in order for CoA conversion and subsequent protein labeling to occur at detectable levels. Rock et al., *J. Biol. Chem.* 275:1377, 2000. *E. coli* has been shown to have a pantetheine import system, the panF symporter, which also may exert some selectivity in the import of analogs and thus influence the ability of pantetheine analogs to be integrated into the CoA pathway in vivo. Jackowski and Alix, *J. Bacteriol.* 172:3842, 1990. However previous studies showed that while overexpression of the panF gene resulted in elevated pantothenate uptake, a concurrent increase in CoA production was not observed, indicating PanK activity as the principal regulator of CoA biosynthesis. With that in mind these kinetic parameters should prove useful for the future design and assay of in vivo carrier protein tags.

Example 23

In Vitro Applications and In Vivo Cell-Surface Labeling of Carrier Protein Fusions The molecules described here have varied applications and provide insight valuable in the expanding field of proteomics. For in vitro applications and in vivo cell-surface labeling of carrier protein fusions, all pantetheine analogs studied herein are efficiently converted into CoA analogs and tethered to the protein via the four-step enzymatic pathway. This alternative methodology negates the purification steps necessary in production of maleimide-CoA analogs from commercial sources, allows almost any variance of the chemical identity of the linker region, and provides an economical substitute for producing large amounts of CoA analogs in cases where large quantities of the desired CoA-maleimide-reporter conjugate may be prohibitively expensive. In addition the expansion of analogs with bioorthogonal reporters allows for increased detection and sensitivity. However despite these subtle advances, it is in the prospect of in vivo labeling that these tools become particularly important. The covalent modifications described herein have practical value in the study of in vivo activity of proteins and a place among the ever increasing myriad of proteomic techniques used to study them.

Of particular importance are the chemoselective ligation reactions demonstrated by the ketone, azide, and alkyne protein labels. These tools allow carrier proteins to be visualized and isolated for the first time without the expense and complication of antibody techniques. While the survey of bioorthogonal coupling partners was not exhaustive, the functionalities introduced should be applicable to other published methods. For instance, one can easily envisage analogs 3 and 5 being modified by Bertozzi's covalent Staudinger ligation with a reporter-conjugated triarylphosphine analog for in vivo applications in which more stringent Cu(I)-catalyzed click chemistry conditions are not ideal. Kohn and Breinbauer, *Angew. Chem. Int. Ed. Engl.* 43:3106, 2004. The PEG-incorporating pantetheine analogs proved non-amenable to in vivo protein labeling, most likely to deletion of a crucial H-bonding interaction. Yet while PEG analogs are often useful for distancing reporter labels from the protein of interest for downstream modification, most likely they are not a necessity in this instance by virtue of the 4'-phosphopantetheine moiety. Indeed the 4'phosphopantetheine is commonly believed to be appended to carrier proteins as a means to distance substrates and products from the protein core, a concept reinforced by recent structural studies of the fatty acid synthase. Simon Jenni et al., *Science* 311:1258, 2006; Maier et al., *Science* 311:1263, 2006.

A detailed investigation of pantetheine analogs has been performed to identify suitable partners for covalent protein labeling inside living cells. A rapid synthesis of pantethenamide analogs was developed for this purpose and used to produce a panel which was evaluated for in vitro and in vivo protein labeling. Kinetic comparisons allowed the construction of a structure-activity relationships to pinpoint the linker, dye, and bioorthogonal reporter of choice for protein labeling. Finally bioorthogonal pantetheine analogs were shown to target carrier proteins with high specificity in vivo and undergo chemoselective ligation to reporters in crude cell lysate. The principal barrier to the utilization of small-molecule probes in cellular contexts is a shortage of site-specific protein labeling methodologies. Chen and Ting, *Curr. Opin. Biotech.* 16:35, 2005. The detailed understanding of the kinetic parameters and structural limitations of pantetheine analogs sets the stage for the routine use of 4'-phosphopantetheine analog labeling in chemical biology.

Abbreviations: CoA, Coenzyme A; PPTase, phosphopantetheinyltransferase; O-GlcNAc, O-linked β-N-acetylglucosamine; β-Ala, β-alanine; PanK, pantothenate kinase; PEG, polyethylene glycol; Pantolactone, (D)-(−)-pantolactone; Boc, tert-butyl carbamate; Alloc, allyl-carbamate; DMACA, 7-dimethylaminocoumarin-4-acetic acid; CP, carrier protein; ACP, fatty acid synthase acyl carrier protein from *E. coli*; VibB, vibriobactin synthase carrier protein from *Vibrio cholerae*; Fren, frenolicin synthase carrier protein from *Streptomyces roseofulvus*.

General procedures for microwave assisted ring-opening of pantolactone, experimental details for the synthesis of compounds 1-18, kinetic, in vitro, and in vivo assay details, full author listings for references 19 and 21 and $^1$H and $^{13}$C-NMR spectra of all final compounds and synthetic intermediates is available free of charge via the Internet at http://pubs.acs.org.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed:

1. A method to generate analogs of coenzyme A, comprising:
   phosphorylating a pantetheine analog or a derivative thereof to form a phosphopantetheine analog or a derivative thereof, the pantetheine analog or derivative thereof comprising a reporter or a bioorthogonal tag having reactivity with a reporter,
   adenylating the phosphopantetheine analog or a derivative thereof to form a dephosphocoenzyme A analog or a derivative thereof, and,
   phosphorylating the 3'-hydroxyl of the dephosphocoenzyme A analog or a derivative thereof to form a coenzyme A analog or a derivative thereof, wherein the phosphorylating of the pantetheine analog or a derivative thereof, the adenylating, or the phosphorylating the 3'-hydroxyl of the dephosphocoenzyme A analog or a derivative thereof is catalyzed by one or more native enzymes.

2. The method of claim 1, wherein the pantetheine analog or derivative thereof comprises three modules.

3. The method of claim 2, wherein the three modules are selected from a ω-functionalized amine, a sidechain, an α-amino acid, a β-amino acid, a linker, and a modulator.

4. The method of claim 3, wherein the ω-functionalized amine, the sidechain, the α-amino acid, the β-amino acid, the linker, or the modulator comprises the reporter or the bioorthogonal tag.

5. The method of claim 3, wherein the modulator is a dihydroxy acid, an aminohydroxy acid, a pantoic acid, or a homolog or derivative of pantoic acid.

6. The method of claim 1, wherein the phosphorylation of the pantetheine analog or derivative thereof is catalyzed by a native enzyme.

7. The method of claim 6, wherein the native enzyme is a kinase.

8. The method of claim 7, wherein the kinase is a pantothenate kinase.

9. The method of claim 1, wherein adenylating the phosphopantetheine analog or derivative thereof is catalyzed by a native enzyme.

10. The method of claim 9, wherein the native enzyme is an adenylyltransferase.

11. The method of claim 10, wherein the adenylyltransferase is phosphopantetheine adenylyltransferase.

12. The method of claim 1, wherein phosphorylating the 3'-hydroxyl of the dephosphocoenzyme A analog or derivative thereof is catalyzed by a native enzyme.

13. The method of claim 12, wherein the native enzyme is a kinase.

14. The method of claim 13, wherein the kinase is a dephospho-CoA kinase.

15. The method of claim 1, further comprising contacting the coenzyme A analog or derivative thereof with a carrier protein domain to form a reporter labeled protein.

16. The method of claim 15, wherein the carrier protein domain comprises a fusion construct between a peptide or carrier protein domain and a protein of interest.

17. The method of claim 15, wherein formation of the reporter labeled protein is catalyzed by a phosphotransferase.

18. The method of claim 17, wherein the phosphotransferase is 4'-phosphopantetheinyltransferase.

19. The method of claim 1, wherein the phosphopantetheine analog or derivative thereof can be used to detect proteins, identify proteins, characterize proteins, inhibit proteins, activate proteins, or examine the structure of proteins.

20. The method of claim 1, wherein the dephosphocoenzyme A analog or derivative thereof can be used to detect proteins, identify proteins, characterize proteins, inhibit proteins, activate proteins, or examine the structure of proteins.

21. The method of claim 1, wherein the coenzyme A analog or derivative thereof can be used to detect proteins, identify proteins, characterize proteins, inhibit proteins, activate proteins, or examine the structure of proteins.

22. The method of claim 1, further comprising contacting the bioorthogonal tag with a reporter, the reporter and the bioorthogonal tag forming a covalent attachment.

23. The method of claim 22, wherein the reporter is attached to the bioorthogonal tag by an azide-alkyne cycloaddition reaction.

24. The method of claim 22, wherein the reporter is attached to the bioorthogonal tag by a ketone-hydroxylamine reaction.

25. The method of claim 22, wherein the reporter is an affinity reporter, a colored reporter, a fluorescent reporter, a magnetic reporter, a radioisotopic reporter, a peptide reporter, a metal reporter, a nucleic acid reporter, a lipid reporter, a glycosylation reporter, a reactive reporter, an enzyme inhibitor, or a biomolecular substrate.

26. The method of claim 1, wherein the reporter is a fluorescent reporter.

27. The method of claim 1, wherein the reporter is a precursor to a fluorescent reporter.

* * * * *

UNITED STATES PATENT AND TRADEMARK OFFICE
CERTIFICATE OF CORRECTION

PATENT NO. : 7,727,738 B2
APPLICATION NO. : 11/485247
DATED : June 1, 2010
INVENTOR(S) : Michael D. Burkart et al.

It is certified that error appears in the above-identified patent and that said Letters Patent is hereby corrected as shown below:

On page 1, in the Abstract, line 9, after the first occurrence of "the", delete "3'-hydrozyl" and insert --3'-hydroxyl--

On page 1, in the Abstract, line 9, after "labeled", delete "dephosphoCoenzume" and insert --dephosphoCoenzyme--

Signed and Sealed this

Fourteenth Day of September, 2010

David J. Kappos
*Director of the United States Patent and Trademark Office*